(12) United States Patent
Lao et al.

(10) Patent No.: US 9,528,147 B2
(45) Date of Patent: Dec. 27, 2016

(54) SEQUENCE AMPLIFICATION WITH LOOPABLE PRIMERS

(71) Applicant: LIFE TECHNOLOGIES CORPORATION, Carlsbad, CA (US)

(72) Inventors: Kai Lao, Pleasanton, CA (US); Neil Straus, Emeryville, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/723,304

(22) Filed: May 27, 2015

(65) Prior Publication Data

US 2015/0322504 A1    Nov. 12, 2015

Related U.S. Application Data

(63) Continuation of application No. 14/177,055, filed on Feb. 10, 2014, now abandoned, which is a continuation of application No. 13/175,595, filed on Jul. 1, 2011, now abandoned, which is a continuation of application No. 12/142,683, filed on Jun. 19, 2008, now abandoned.

(60) Provisional application No. 60/954,299, filed on Jun. 20, 2007.

(51) Int. Cl.
  *C12Q 1/68* (2006.01)
  *C07H 21/04* (2006.01)
  *C07H 21/02* (2006.01)

(52) U.S. Cl.
  CPC ........... *C12Q 1/6853* (2013.01); *C12Q 1/6848* (2013.01); *C12Q 1/6876* (2013.01)

(58) Field of Classification Search
  None
  See application file for complete search history.

(56) References Cited

U.S. PATENT DOCUMENTS

| | | |
|---|---|---|
| 6,403,319 B1 | 6/2002 | Lizardi et al. |
| 7,176,002 B2 | 2/2007 | Lao et al. |
| 2003/0165859 A1 | 9/2003 | Nazarenko et al. |
| 2004/0175733 A1 | 9/2004 | Andersen et al. |
| 2005/0266418 A1 | 12/2005 | Chen et al. |
| 2006/0014190 A1 | 1/2006 | Hennessy |
| 2006/0078906 A1 | 4/2006 | Chen et al. |
| 2006/0078924 A1 | 4/2006 | Finn et al. |
| 2006/0105348 A1 | 5/2006 | Lee et al. |
| 2008/0161197 A1 | 7/2008 | Lao |
| 2009/0023190 A1 | 1/2009 | Lao et al. |
| 2009/0291475 A1 | 11/2009 | Lao et al. |

OTHER PUBLICATIONS

Church, George M., "Genomes for ALL", *Scientific American*, Jan. 2006, 47-54.
Dean, F., et al., "Comprehensive human genome amplification using multiple displacement amplification", *PNAS*, vol. 99(8), 2002, pp. 5261-5266.
Diatchenko, et al., "Supression substractive hybridization: A method for generating differentially regulated or tissue-specific cDNA probes and libraries", *Proc. Natl. Acad. Sci. USA*, 93, Jun. 1996, 6025-6030.
Genomeplex® Whole Genome Amplification: Importing Method Files for the Biomek® FX (Beckman Coulter), Product Information sheet, Sigma®, 3 pages, 2006.
Lao, et al., "Whole genome amplification using single-primer PCR", *Biotechnol. J.*, 3, 2008, 378-382.
Raghunathan, et al., "Genomic amplification from a single bacterium", *Appl. Environ. Microbiol.*, 71, 2005, 3342-3347.
Siebert, et al., "An improved PCR method for walking in uncloned genomic DNA", *Nucleic Acids Research*, 23(6), 1995, 1087-1088.
Tang, F., et al., "mRNA-Seq whole-transcriptome analysis of a single cell", *Nat Methods*, vol. 6(5), 2009, pp. 377-382.
Technical Note: Using Whole-Genome Amplified (WGA) DNA Samples in the GoldenGate® Genotyping Assay. Illumina ® SNP Genotyping, © 2005, 4 pages.
Whole Genome Amplification, Wikipedia entry dated Feb. 4, 2008, accessed at http://en.wikipedia.org/wiki/Whole_genome amplification, 2008.
Zhang, et al., "Sequencing genomes from single cells by polymerase cloning", *Nat. Biotechnol.*, 24, 2006, 680-686.
Zhang, et al., "Whole genome amplification from a single cell: Implications for Genetic analysis", *Proc. Natl. Acad. Sci. USA*, 89, Jul. 1992, 5847-5851.

*Primary Examiner* — David Thomas

(57) ABSTRACT

The present disclosure relates to the amplification of target nucleic acid sequences. This can be accomplished via the use of various primers. The use of these primers, as described herein, results in nucleic acid structures that can reduce the amplification of nonspecific hybridization events (such as primer dimerization) while allowing the amplification of the target nucleic acid sequences.

6 Claims, 17 Drawing Sheets

SEQUENCE LISTING

```
<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
gtcgactgcg tggagtcggc tttttttttt                               30

<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2
tcatgatccg tggagtcggc tttttttttt                               30

<210> SEQ ID NO 3
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (39)...(46)
<223> OTHER INFORMATION: N=degenerate nucleotide

<400> SEQUENCE: 3
tcatgatccg tggagtcggc tttttttttt gatcatgann nnnnnn             46

<210> SEQ ID NO 4
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (39)...(44)
<223> OTHER INFORMATION: N=degenerate nucleotide

<400> SEQUENCE: 4
tcatgatccg tggagtcggc tttttttttt gatcatgann nnnn               44

<210> SEQ ID NO 5
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (39)...(46)
<223> OTHER INFORMATION: N=degenerate nucleotide

<400> SEQUENCE: 5
gtcgactgcg tggagtcggc tttttttttt cagtcgacnn nnnnnn             46

<210> SEQ ID NO 6
<211> LENGTH: 44
<212> TYPE: DNA
<213> ORGANISM: Artificial Sequence
```

```
<220> FEATURE:
<223> OTHER INFORMATION: Primer
<220> FEATURE:
<221> NAME/KEY: misc_feature
<222> LOCATION: (39)...(44)
<223> OTHER INFORMATION: N=degenerate nucleotide

<400> SEQUENCE: 6
gtcgactgcg tggagtcggc tttttttttt cagtcgacnn nnnn          44
```

SEQUENCE AMPLIFICATION WITH LOOPABLE PRIMERS

RELATED APPLICATIONS

The present application is a continuation of U.S. non-provisional application Ser. No. 14/177,055, filed Feb. 10, 2014, which is a continuation of U.S. non-provisional application Ser. No. 13/175,595, filed Jul. 1, 2011 and now abandoned, which is a continuation of U.S. non-provisional application Ser. No. 12/142,683, filed Jun. 19, 2008 and now abandoned, which claims the filing date benefit of U.S. Provisional Application No. 60/945,299, filed Jun. 20, 2007. The contents of each of the foregoing patent applications are incorporated by reference in their entirety.

SEQUENCE LISTING

The present application is being filed along with a Sequence Listing in electronic format. The Sequence Listing is provided as a file entitled ABIOS-073A.TXT, created Jun. 17, 2008, which is 1.53 Kb in size. The information in the electronic format of the Sequence Listing is incorporated herein by reference in its entirety.

FIELD

The invention relates to methods and compositions for amplifying nucleic acid sequences.

INTRODUCTION

Whole genome amplification (WGA) can be a valuable technique for amplification of a genome from minimal or limiting amounts of DNA for subsequent molecular genetic analysis.

Whole genome amplification can be performed using either conventional or nonconventional PCR amplification methods. Conventional PCR entails the amplification and subsequent detection of specific DNA sequences which are precisely characterized in length and sequence using non-degenerate primers, while random, "non-conventional" PCR involves universal amplification of prevailing DNA or amplification of unknown intervening sequences which are not generally defined in length or sequence using degenerate primers.

SUMMARY

Some of the present embodiments allow target nucleic acid sequences to be amplified using at least one loopable primer. In some embodiments, the loopable primer includes a random or degenerate region. In some embodiments, a nucleic acid sequence within the loopable primer includes a universal region and/or a noncomplementary region to reduce the likelihood of nonspecific hybridization of the primer (such as primer dimers) during subsequent amplification steps.

A loopable primer can include a random region, a first loop forming region, a universal region, optionally a non-complementary region, and a second loop forming region. The first and second loop forming regions include nucleic acid sequences that allow the regions to hybridize to one another. The noncomplementary region is located between the first and second loop forming regions. The universal region is positioned between the two loop forming regions. The noncomplementary region and the universal region can be configured so that a sequence associated with a target sequence that has been amplified by the loopable primer (a double-extended loopable primer) forms a self-hybridized structure involving the noncomplementary region and/or the universal region. This self-hybridized structure can allow for the selective amplification of longer sections of target nucleic acid sequence over shorter sections. The presence of the noncomplementary region can assist in reducing non-specific binding of various primers throughout the amplification process. The loopable primer can include sequences and structures in addition to those listed above.

In some aspects, a self-hybridized nucleic acid sequence in a PCR amplification mixture is provided. The self-hybridized nucleic acid sequence includes a first loop forming region, a universal region, an additional first loop forming region, a random region, a second loop forming region, a sequence that is complementary to the noncomplementary region, a sequence that is complementary to the universal priming site, and an additional second loop forming region.

In some embodiments, the present disclosure provides a nucleic acid sequence. The nucleic acid sequence can comprise a 3' target specific region, a first loop forming region, a universal region, and a second loop forming region. The first and second loop forming regions comprise a set of nucleic acid sequences that are configured to hybridize to one another. The universal region is located between the first and second loop forming regions. The universal region is configured so that the nucleic acid sequence can form a self-hybridized structure comprising the universal region, the first loop forming region, and the second loop forming region on subsequent amplifications.

In some embodiments, the present disclosure provides a self-hybridizable DNA structure in a PCR amplification mixture. The self-hybridizable DNA structure can comprise a first loop forming region, a universal region connected to the first loop forming region, a second loop forming region connected to the universal region, and a first 3' target specific region connected to the second loop forming region. The structure can also comprise a sequence that is complementary to a second 3' target specific region, wherein the sequence that is complementary to the second 3' target specific region is part of a same nucleic acid strand as the first 3' target specific region. The structure can also comprise a sequence that is complementary to the second loop forming region, wherein the sequence that is complementary to the second loop forming region is connected to the sequence that is complementary to the second 3' target specific region. The structure can also comprise a sequence that is complementary to the universal region, wherein the a sequence that is complementary to the universal region is connected to the sequence that is complementary to the second loop forming region. The structure can also comprise a sequence that is complementary to the first loop forming region, wherein the sequence that is complementary to the first loop forming region is connected to the sequence that is complementary to the universal region.

In some embodiments, the present disclosure provides a method for nucleic acid amplification. The method can comprise allowing a 3' target specific region of a loopable primer to hybridize to a first part of a target nucleic acid sequence. A loop in the loopable primer is configured to allow the 3' end of the loopable primer to hybridize to a first part of the target nucleic acid sequence without the remainder of the loopable primer annealing to the target nucleic acid sequence. The loopable primer further comprises a first loop forming region, a universal region, and a second loop forming region. The first and second loop forming regions comprise nucleic acid sequences that hybridize to one another. The universal region is located between the first and second loop forming regions. The method further comprises extending the loopable primer that is hybridized to the target nucleic acid sequence to form an extended loopable primer, allowing an additional loopable primer to hybridize to a complementary part of the target nucleic acid sequence on the extended loopable primer, and extending the loopable primer to form a double-extended loopable primer.

In some embodiments, the present disclosure provides a nucleic acid sequence comprising a 3' target specific region, a first loop forming region, a universal region, a noncomplementary region, and a second loop forming region. The first and second loop forming regions comprise a set of nucleic acid sequences that are configured to hybridize to one another. The universal region is located between the first and second loop forming regions. The noncomplementary region is located between the first and second loop forming regions. The universal region is configured so that a sequence associated with a target sequence that has been amplified by the nucleic acid sequence can form a self-hybridized structure comprising the universal region, the noncomplementary region, the first loop forming region, and the second loop forming region on subsequent amplifications. The nucleic acid is created by deliberately selecting the sequence of the first loop forming region so that it hybridizes to the second loop forming region. The nucleic acid is created by deliberately selecting a universal region.

In some aspects, a method for nucleic acid amplification is provided. The method includes allowing a 3' target specific region of a loopable primer to hybridize to a first part of a target sequence. A loop in the loopable primer is configured to allow the 3' target specific region of the loopable primer to hybridize to the first part of the target sequence without the remainder of the loopable primer annealing to the target sequence. The loopable primer can include the following: a random region, a first loop forming region, a noncomplementary region, and a second loop forming region. The loopable primer can also include a universal region. The first and second loop forming regions include nucleic acid sequences that are able to hybridize to one another. The noncomplementary region is located between the first and second loop forming regions. The method can further include extending the loopable primer to form an extended loopable primer, allowing an additional loopable primer to hybridize to a complementary part of the target sequence on the extended loopable primer, and extending the additional loopable primer to form a double-extended loopable primer. The additional loopable primer can be the same or different from the first loopable primer.

DETAILED DESCRIPTION OF VARIOUS EMBODIMENTS

Figure 1A:
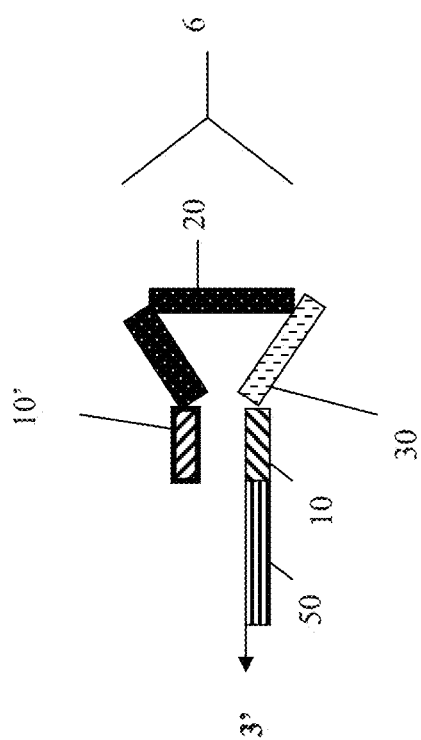
FIG. 1A is a depiction of one embodiment of a loopable primer

The use of loopable primers in the amplification of a target nucleic acid sequence is described herein. In some embodiments, this relates to the realization that one problem that occurs in target nucleic acid amplification is inadvertent primer dimerization and/or spurious internal priming. This can be of concern when random priming regions, degenerate priming regions, universal priming regions, or some combination thereof are used, especially in multiplexed embodiments. In such embodiments, large numbers of various primer sequences are used, which increases the likelihood that undesired priming (e.g. such as primer dimers) will occur.

In some embodiments, this issue has been addressed through the use of loopable primers that include a universal region and optionally a noncomplementary region within the loop of the loopable primer. In some embodiments, this results in the more efficient amplification of target nucleic acid sequences. Some embodiments of the technique can also reduce the effect of spurious internal priming. In some embodiments, the noncomplementary region within the looped section of the primer can reduce the likelihood that inadvertent primer dimerization will occur. In some embodiments, the target nucleic acid sequence is genomic DNA. In some embodiments, the method can be applied to allow for more efficient amplification of large amounts of gDNA, such as for whole genome amplification. The above as well as additional embodiments are described in greater detail following the definition and alternative embodiments section provided below.

Some Definitions and Alternative Embodiments

As used herein, the term "target nucleic acid sequence" refers to a polynucleotide sequence that is sought to be detected in a sample. The target nucleic acid sequence can be obtained from any source and can include any number of different compositional components. For example, the target can be nucleic acid (e.g. DNA or RNA), transfer RNA, siRNA, and can include nucleic acid analogs or other nucleic acid mimics. The target can be methylated, non-methylated, or both. The target can be bisulfite-treated and non-methylated cytosines converted to uracil. Further, it will be appreciated that "target nucleic acid sequence" can refer to the target nucleic acid sequence itself, as well as surrogates thereof, for example amplification products, and native sequences. In some embodiments, the target nucleic acid sequence is a miRNA molecule. In some embodiments, the target nucleic acid sequence lacks a poly-A tail. In some embodiments, the target nucleic acid sequence is a short DNA molecule derived from a degraded source, such as can be found in, for example but not limited to, forensics samples (see for example Butler, 2001, Forensic DNA Typing: Biology and Technology Behind STR Markers). In some embodiments, the target nucleic acid sequences of the present teachings can be present or derived from any of a number of sources, including without limitation, viruses, prokaryotes, eukaryotes, for example but not limited to plants, fungi, and animals. These sources can include, but are not limited to, whole blood, a tissue biopsy, lymph, bone marrow, amniotic fluid, hair, skin, semen, biowarfare agents, anal secretions, vaginal secretions, perspiration, saliva, buccal swabs, various environmental samples (for example, agricultural, water, and soil samples), research samples generally, purified samples generally, cultured cells, and lysed cells.

It will be appreciated that target nucleic acid sequences can be isolated or obtained from samples using any of a variety of procedures known in the art, for example the Applied Biosystems ABI Prism™ 6100 Nucleic Acid Prep-Station, and the ABI Prism™ 6700 Automated Nucleic Acid Workstation, Boom et al., U.S. Pat. No. 5,234,809, mirVana RNA isolation kit (Ambion), etc. It will be appreciated that target nucleic acid sequences can be cut or sheared prior to analysis, including the use of such procedures as mechanical force, sonication, restriction endonuclease cleavage, or any method known in the art. Cleaving can be done specifically or non-specifically. In general, the target nucleic acid sequences of the present teachings will be single stranded, though in some embodiments the target nucleic acid sequence can be double stranded, and a single strand can result from denaturation. In some embodiments, the target nucleic acid sequence is genomic DNA.

As will be appreciated by one of skill in the art, the term "target nucleic acid sequence" can have different meanings at different steps throughout the method. For example, in an initial sample, there can be a target nucleic acid sequence that is 2 kb in length. When this is amplified by the loopable primer to form a double-extended loopable primer, part of the target nucleic acid sequence can be contained within the double-extended loopable primer; however, not all of the target nucleic acid sequence need be contained within the double-extended loopable primer. Regardless of this, the section of the target nucleic acid sequence that is amplified can still be referred to as the "target nucleic acid sequence" (in part because it will still indicate the presence or absence of the large target nucleic acid sequence of which it is a part). Similarly, when the section of the insert section, which contains the target nucleic acid sequence, is amplified by the insert amplification primers it can also be described as amplifying the "target nucleic acid sequence." One of skill in the art will appreciate that, likely, the length of the target nucleic acid sequence will decrease as the sequence is processed further. If necessary, each target nucleic acid sequence in each step can be specifically designated as an "initial target nucleic acid sequence," a "double-extended loopable primer target nucleic acid sequence", and a "insert section target nucleic acid sequence." Additionally, one of skill in the art will appreciate that the sequence that one is interested in determining if present in a sample can be a separate sequence from a target nucleic acid sequence that is amplified. For example, the sequences can be in linkage disequilibrium or from a different part of a gene or stretch of nucleic acids. Such sequences can be termed "inquiry target nucleic acid sequences."

As used herein, the term "loopable primer" refers to a molecule comprising a 3' target specific portion, a stem (comprising a first loop forming region and a second loop forming region), and a loop portion. Illustrative loopable primers are depicted in FIG. 1A and elsewhere in the present teachings. It will be appreciated that the loopable primers can be comprised of ribonucleotides, deoxynucleotides, modified ribonucleotides, modified deoxyribonucleotides, modified phosphate-sugar-backbone oligonucleotides, nucleotide analogs, or combinations thereof. For some illustrative teachings of various nucleotide analogs etc, see Fasman, 1989, Practical Handbook of Biochemistry and Molecular Biology, pp. 385-394, CRC Press, Boca Raton, Fla., Loakes, N. A. R. 2001, vol 29:2437-2447, and Pellestor et al., Int J Mol. Med. 2004 April; 13(4):521-5), references cited therein, and recent articles citing these reviews. It will be appreciated that the selection of the loopable primers to query a given target nucleic acid sequence, and the selection of which collection of target nucleic acid sequence sequences to query in a given reaction with which collection of loopable primers, will involve procedures generally known in the art, and can involve the use of algorithms to select for those sequences with minimal secondary and tertiary structure, those targets with minimal sequence redundancy with other regions of the genome, those target regions with desirable thermodynamic characteristics, and other parameters desirable for the context at hand. In some embodiments, the loop section includes one or more additional nucleic acids that serve a desired function. In some embodiments, a universal primer is included within the loop. In some embodiments, a noncomplementary region or sequence is included within the loop. In some embodiments, an identifying portion is included within the loop.

As will be appreciated by one of skill in the art, even though a primer is "loopable" it may not always be in its looped form. For example, at high temperatures or salt conditions, the two loop forming regions can separate from one another. However, even in situations where the loopable primer is not actually looped, it can still be referred to as a "loopable primer." Thus, the term "loopable primer" does not require that the primer actually be in the looped configuration.

As used herein, the term "3' target-specific portion" refers to a single stranded portion of a loopable primer that is complementary to at least a portion of a target nucleic acid sequence. The 3' target-specific portion is located downstream from the stem of the loopable primer. Generally, the 3' target-specific portion is between 4 and 15 nucleotides long and can be between 6 and 12 nucleotides in length. In some embodiments, the 3' target-specific portion is 7 nucleotides long. It will be appreciated that routine experimentation can be used to optimize length, and that 3' target-specific portions that are longer than 8 nucleotides or shorter than 6 nucleotides are also contemplated by the present teachings. In some embodiments, modified bases such as LNA can be used in the 3' target specific portion to increase the stability, for example by increasing the Tm of the loopable primer (see for example Petersen et al., Trends in Biochemistry (2003), 21:2:74-81). In some embodiments, universal bases can be used in the 3' target specific portion, for example to allow for smaller libraries of loopable primers. Universal bases can also be used in the 3' target specific portion to allow for the detection of unknown targets (e.g. targets for which specific binding sequences are not known). For some descriptions of universal bases, see for example Loakes et al., Nucleic Acids Research, 2001, Volume 29, No. 12, 2437-2447. In some embodiments, modifications including but not limited to LNAs and universal bases can improve reverse transcription specificity and potentially enhance detection specificity.

In some embodiments, the 3' target-specific region includes or is a degenerate region, a random region, a specific region, or a known sequence. In some embodiments, the 3' target specific region includes a combination of these regions. In some embodiments, the 3' target specific regions have a Tm of between about 10° C. and 50° C. In some embodiments, a 15-mer has a Tm of less than about 60° C.

The term "degenerate primer" when used herein refers to a mixture of similar primers with differing bases at the varying positions (Mitsuhashi M, J Clin Lab Anal, 10(5):285 93 (1996); von Eggeling et al., Cell Mol Biol, 41(5):653 70 (1995); (Zhang et al., Proc. Natl. Acad. Sci. USA, 89:5847 5851 (1992); Telenius et al., Genomics, 13(3):718 25 (1992)). Such primers can include inosine as inosine is able to base pair with adenosine, cytosine, guanine or thymidine. Degenerate primers allow annealing to and amplification of a variety of target sequences that can be related. Degenerate primers that anneal to target DNA can function as a priming site for further amplification. A degenerate region is a region of a primer that varies, while the rest of the primer can remain the same. Degenerate primers (or regions) denote more than one primer and can be random. A random primer (or regions) denotes that the sequence is not selected, and it can be degenerate. In some embodiments, the 3' target specific regions have a Tm of between about 10° C. and 50° C. In some embodiments, a 15-mer has a Tm of less than about 60° C.

A "specific region" (in contrast to a "3' target specific region" which is a broader genus) is able to bind to a specific genomic sequence occurring in the human genome with a specific frequency. In some embodiments, this frequency is between about 0.01% and 2.0%, such as, for example, between about 0.05% and 0.1% or between about 0.1% and 0.5%. In some embodiments, the length of the "specific region" of a primer depends mainly on the averaged lengths of the predicted PCR products based on bioinformatic calculations. The definition includes, without limitation, a "specific region" of between about 4 and 12 bases in length. In more particular embodiments, the length of the 3' specific region can, for example, be between about 4 and 20 bases, or between about 8 and 15 bases. Specific regions having a Tm of between about 10° C. and 60° C. are included within the definition. The term, "specific primer," when used herein refers to a primer of specified sequence. An example of a specific region would be a region for priming for the amplification of a STR locus.

The term "random region" as used herein refers to a region of an oligonucleotide primer that is able to anneal to unspecified sites in a group of target sequences, such as in a genome. The "random region" facilitates binding of the primer to target DNA and binding of the polymerase enzyme used in PCR amplification to the duplex formed between the primer and target DNA. The random region nucleotides can be degenerate or non-specific, promiscuous nucleobases or nucleobase analogs. The length of the "random region" of the oligonucleotide primer, among other things, depends on the length of the specific region. In certain embodiments, without limitation, the "random region" is between about 2 and 15 bases in length, between about 4 and 12 bases in length or between about 4 and 6 bases in length.

In some embodiments, the 3' target-specific portion comprises both a specific region and a random region or degenerate region. In other embodiments, the 3' target-specific portion includes a specific region, a random region or a degenerate region. In other embodiments, the 3' target specific region of the loopable primer only includes a specific region, a random region, or a degenerate region.

In some embodiment, the specific and random regions combined will be about 9 bases in length, e.g., if the specific region has 4 bases, the random region will have 5 bases.

As used herein, the term "stem" refers to the double stranded region of a loopable primer that is between the 3' target-specific portion and the loop. Generally, the stem is between 6 and 20 nucleotides long (that is, 6-20 complementary pairs of nucleotides, for a total of 12-40 distinct nucleotides). In some embodiments, the stem is 8-14 nucleotides long. Those in the art will appreciate that stems shorter than 6 nucleotides and longer than 20 nucleotides can be identified in the course of routine methodology and without undue experimentation, and that such shorter and longer stems are contemplated by the present teachings. In some embodiments, the stem can comprise an identifying portion. In some embodiments, the stem includes a first loop forming region and a second loop forming region, which, when hybridized together, create the stem structure.

As used herein, the term "loop" in reference to the loopable primer refers to a region of the loopable primer that is located between the two complementary strands of the stem, e.g. as depicted in FIG. 1A. Typically, the loop includes single stranded nucleotides, though other moieties modified DNA or RNA, Carbon spacers such as C18, and/or PEG (polyethylene glycol) can also be included in the loop. Generally, the loop is between 4 and 20 nucleotides long. In some embodiments, the loop is between 14 and 18 nucleotides long. In some embodiments, the loop is 16 nucleotides long. Those in the art will appreciate that loops shorter that 4 nucleotides and longer than 20 nucleotides can be identified in the course of routine methodology and without undue experimentation, and that such shorter and longer loops are contemplated by the present teachings. In some embodiments, the loop can comprise an identifying portion. As will be appreciated by one of skill in the art, the section of the nucleic acid sequence that forms the loop need not always be in a loop.

As used herein, the "first loop forming region" refers to a nucleic acid sequence which includes a sequence that is capable of hybridizing to a second loop forming region in the same loopable primer, via intramolecular hybridization. This hybridization can form the looped section of the loopable primer. As will be appreciated by one of skill in the art, the length of the first loop forming region can vary. In some embodiments, the first loop forming region is between 5 and 20 nucleic acids long. In some embodiments, the stem length is long enough to form a stable looped structure at the annealing temperature. In some embodiments, melting point of the first loop forming region hybridized to the second loop forming region is about 10° C. to 20° C. higher than the annealing temperature of the 3' target specific region. For example, in embodiments in which annealing is performed at 35° C., an 8 base stem can be used that has a 55° C. Tm.

As will be appreciated by one of skill in the art, in some embodiments, the melting point is high enough so that the loopable primer is in a loop form during hybridization to the target sequence. In some embodiments, the melting point is low enough so that the loopable primer can linearize during various extension steps. In some embodiments, the first and second loop forming regions, when hybridized together, have a Tm that is at least above the former temperature and at least at or below the latter temperature. In some embodiments, the melting point is low enough to allow the universal primer to anneal to the template. In some embodiments, the Tm is below 70° C.

As used herein, the "second loop forming region" refers to a nucleic acid sequence that includes a sequence that is configured for and therefore capable of hybridizing to a first loop forming region in the same nucleic acid segment, via intramolecular hybridization under particular conditions.

As used herein, the "noncomplementary region" refers to nucleic acid sequence in a loopable primer or product thereof. In some embodiments, the noncomplementary region is located between the first and second loop forming regions. In some embodiments, the noncomplementary region is a sequence that is present in at least some of the various primers or sequences in a reaction mixture. In some embodiments, the sequence is common in all or less than all of the primers used, for example 100, 100-99, 99-95, 95-90, 90-80, 80-70, 70-60, 60-50, 50-40, 40-30, 30-20, 20-10, 10-5, 5-1, 1% or less. Thus, in some embodiments, the primers for the target amplification all contain the same noncomplementary sequence. In some embodiments, the primers in subsequent steps (or a percent as noted above) also have the same noncomplementary region. As will be appreciated by one of skill in the art, the presence of similar sequences across various primers will reduce the likelihood that primer dimerization will occur (as the primers will be less likely to hybridize to one another). In some embodiments, the noncomplementary region is noncomplementary with respect to sequences in the target nucleic acid sequence. This embodiment is described in more detail below. In some embodiments, the noncomplementary region is both present in various primers (thereby reducing primer dimerization) and noncomplementary to sequences in the target sequences (e.g. a relatively long series of thymines)

The presence of the noncomplementary sequence need not absolutely prevent the occurrence of primer dimerization or other forms of nonspecific hybridization in every situation. In some embodiments, the presence of the noncomplementary region reduces the likelihood of these undesired forms of hybridization from occurring. In some embodiments, any decrease is sufficient, for example, less than 100% of the dimers that would have occurred without the noncomplementary region, e.g. 100-99, 99-98, 98-95, 95-90, 90-80, 80-70, 70-60, 60-50, 50-40, 40-30, 30-20, 20-10, 10-5, 5-1, or less of the original primer dimers will occur when the noncomplementary region is present in the loopable primer. In some embodiments, the presence of the noncomplementary region decreases likelihood of nonspecific amplification or amplification of undesirably small sections of target nucleic acid sequence. Additionally, while the noncomplementary sequence can be the same in all of the primers or loopable primers used, it need not be the same. For example, in some embodiments, the noncomplementary regions, while not hybridizing, are not the same sequences (e.g., TTTT vs. CCCC). In other embodiments, the noncomplementary regions are similar, but not identical, (e.g., TTTT vs. TTTC). In other embodiments, the noncomplementary regions are completely different types or sequences of nucleic acids; however, they will still reduce the likelihood of various forms of nonspecific hybridization. As will be appreciated by one of skill in the art, the length of the noncomplementary region can vary and the length required can depend on the various reaction conditions and the sequences present in the target sample, issues that can readily be determined by one of skill in the art.

In some embodiments, the noncomplementary region is effective at reducing the nonspecific hybridization of an amplification primer. The amplification primer can have a region that hybridizes to the noncomplementary region (as well as a region that can hybridize to the universal region). Thus, the amplification primer can be more specific for the double-extended loopable primer products rather than other nonspecific priming events that could occur if the amplification primer only contained a universal region. Thus, in some embodiments, the presence of the noncomplementary region in the loopable primer can assist in reducing subsequent nonspecific amplification.

In some embodiments, the noncomplementary region is at least 3-15 nucleic acids in length. In some embodiments, the noncomplementary region comprises a series of thymine nucleic acids. In some embodiments, the noncomplementary region is 8-12 thymines. In some embodiments, the noncomplementary region only includes 3, 4, 5, 6, 7, 8, 9, 10, 11, 12, 13, 14, 15, 16, 17, 18, 19, or 20 thymines (T) or adenines (A) or similar nucleic acids (such as artificial nucleic acids).

As will be appreciated by one of skill in the art, while the term "noncomplementary" can denote that the sequence does not significantly or functionally complement another sequence in a mixture, there will be sequences that can hybridize to the noncomplementary region. For example, in a double-extended loopable primer (FIG. 3) there is both the noncomplementary region 30 and the complement to the noncomplementary region 30'. Additionally, as noted above, in some embodiments, the amplification primer can also include a sequence that can hybridize to the noncomplementary region.

The term "does not effectively hybridize" denotes that the amount of hybridization that occurs is sufficient so that a significant reduction in primer dimerization or other forms of nonspecific hybridization occurs. As will be appreciated by one of skill in the art.

As used herein, the "target binding site" refers to a nucleic acid sequence, in the target nucleic acid sequence, where the 3' target-specific portion of the loopable primer can or is configured to hybridize to. As will be appreciated by one of skill in the art, this section can be part of the target nucleic acid sequence and can therefore be gDNA or other nucleic acid sequences.

As used herein, the "extended loopable primer" refers to a nucleic acid sequence that has been extended from a loopable primer hybridized to a target binding site. The extended loopable primer can include the loopable primer, along with a sequence that is effectively complementary to a sequence that is contained within the target sequence (in addition to the target binding sequence). In some embodiments, the extended portion of the extended loopable primer is at least 100 nucleic acids in length. In some embodiments, the extended portion is at least 200 nucleic acids in length. In some embodiments, the extended portion is not more than 10 kb in length. However, in other embodiments, other lengths are contemplated. As will be appreciated by one of skill in the art, the "extended loopable primer" will include a loopable primer; however, it will not need to serve as a primer itself. In some embodiments the loopable primer portion of it is still looped, although this is not required.

As used herein, the "loopable primer complement" refers to a nucleic acid sequence that is the complement of the loopable primer (of course, the loopable primer complement need not be 100% complementary, as the 3' target specific regions can include degenerate or random regions). As will be appreciated by one of skill in the art, the sequence of the loopable primer complement can still form a looped primer itself. Additionally, any universal region and/or noncomplementary region in the loopable primer complement will be complementary to the relevant section in the loopable primer. An example of a loopable primer complement can be found in FIG. 3, on the right hand side of sequence 4, including sections 10, 20', 30', 10', and 52. However, as noted above, a loopable primer complement need not have a complementary 3' target specific region to the 3' target specific region in the loopable primer (as these can be from different initial loopable primers.

As used herein, the "universal region complement" refers to a nucleic acid sequence that is the complement of the universal region.

The term "double extended looped primer" refers to a nucleic acid sequence that has been formed by extending a loopable primer that is hybridized to an extended loopable primer. In other words, the nucleic acid sequence has been extended twice via loopable primers. In some embodiments, the term "double extended looped primer" simply means that there is a nucleic acid sequence that includes a loopable primer, a target sequence, and a loopable primer complement; the method by which it is made is not relevant. In some embodiments, the term "double extended looped primer" simply means that there is a nucleic acid sequence that includes a universal region, a target sequence, and a universal region complement; the method by which it is made is not relevant. As will be appreciated by one of skill in the art, the "double-extended loopable primer" can include a loopable primer and a loopable primer complement; however, it does not necessarily to serve as a primer itself. In some embodiments the loopable primer portion of it is still looped, although this is not required.

Figure 3:
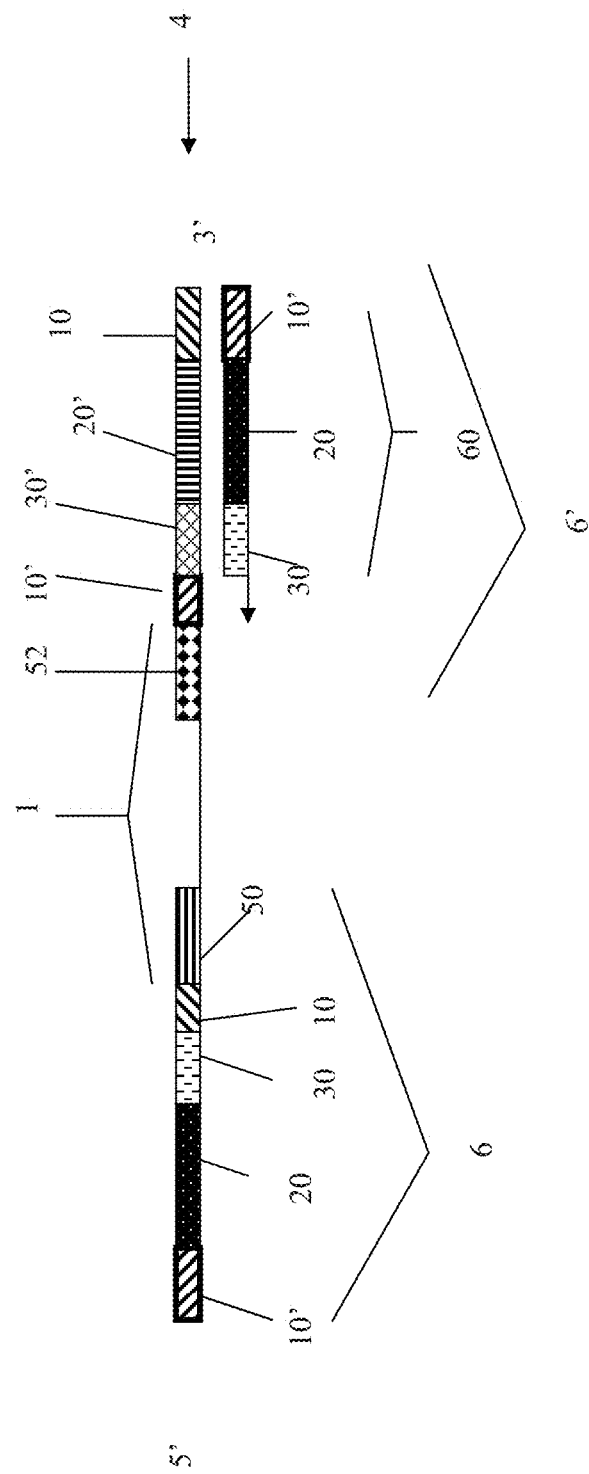
FIG. 3 is a depiction of some embodiments involving amplification primers.

The "amplification primer" primer need not be looped. An Example of such a primer is depicted in FIG. 3, as 60. In some embodiments, the amplification primer is a linear primer. In some embodiments, the amplification primer is not complementary to the loopable primer. In some embodiments, the amplification primer has at least some of the same sequence as the loopable primer. In some embodiments, the amplification primer includes a sequence that is the same as the universal region. In some embodiments, the amplification primer includes a sequence that is the same as the noncomplementary region. In some embodiments, the amplification primer includes a sequence that is the same as the universal region. In some embodiments the amplification primer further includes a sequence that is the same as the second loop forming region. In some embodiments, the amplification primer includes the second loop forming region, the universal region, and (optionally) the noncomplementary region. As will be appreciated by one of skill in the art, the sequences need not be identical in all embodiments, as sequences that still selectively hybridize to the desired location can be employed as well. In some embodiments, the amplification primer is between 10-40 nucleotides long, such as a 30-mer. In some embodiments the amplification primer is 14 nucleotides long. In some embodiments, the amplification primer includes a "universal reverse primer," which indicates that the sequence of the reverse primer can be used in a plurality of different reactions querying different target nucleic acid sequences, but that the amplification primer nonetheless can be the same sequence. In some embodiments, the amplification primer includes a tail region that is not complementary to the sequence that the rest of the primer hybridizes to.

Figure 4:
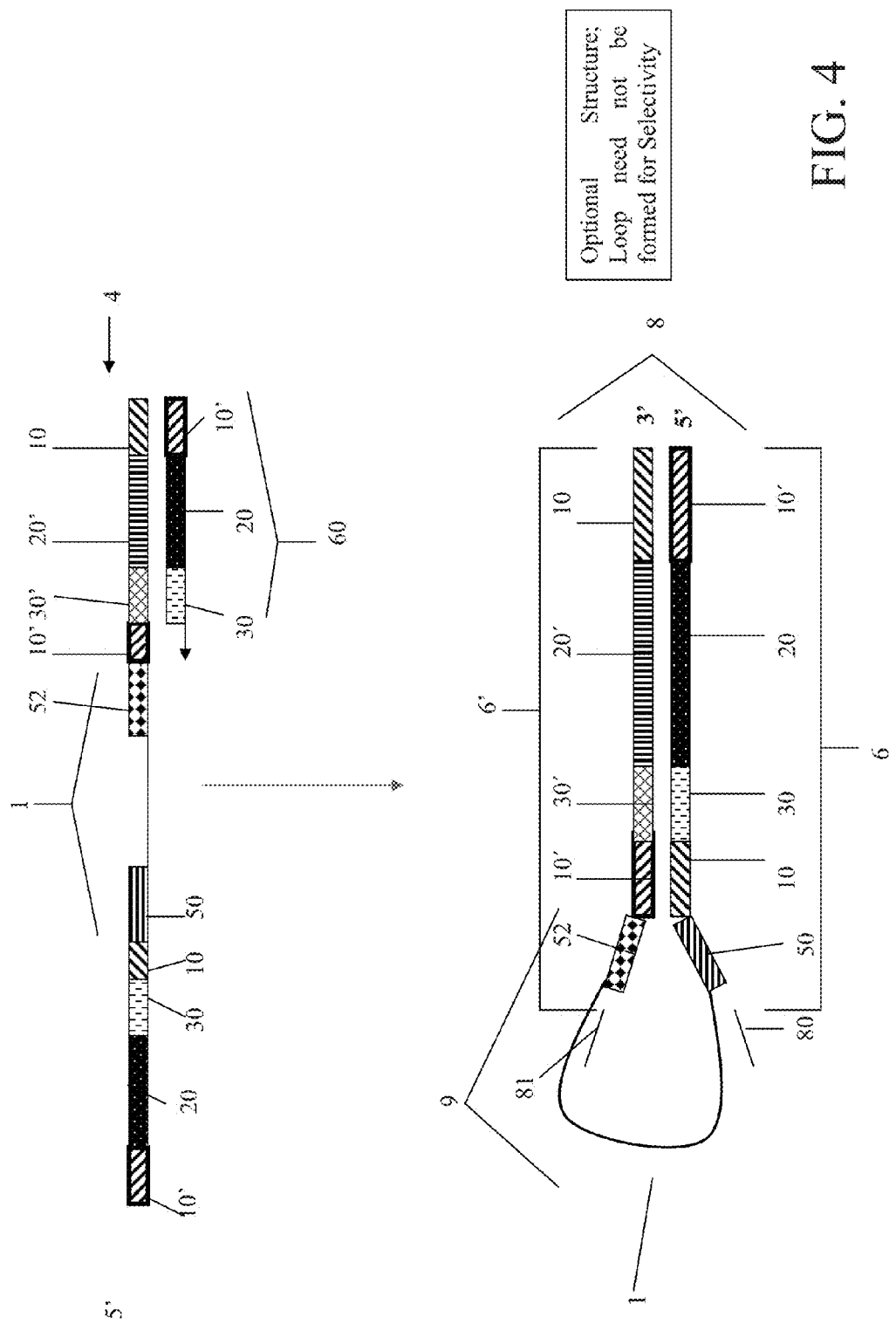
FIG. 4 is a depiction of some embodiments in which a double-extended loopable primer is self-hybridized.
Figure 5:
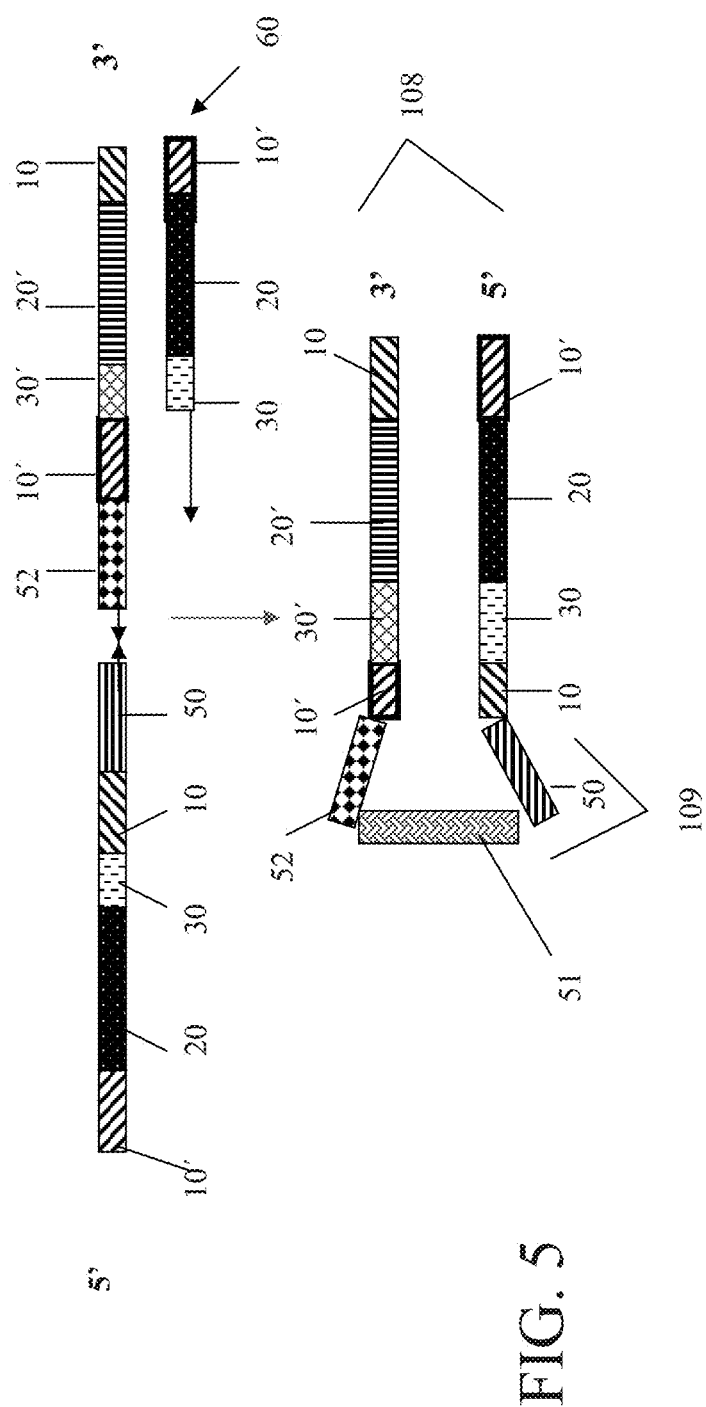
FIG. 5 is a depiction of some embodiments in which a double-extended loopable primer is self-hybridized.

The term "insert section" or "insert target" or "capture section" refers to the section from one 3' target specific region to a second 3' target specific region, as shown in FIG. 4. In some embodiments, the insert section includes the 3' target specific region as well; thus, the insert section includes 52 and 50 in FIG. 4, and is defined between the first loop forming region 10 and the second loop forming region 10'. The insert section 9 can include a significant portion of target nucleic acid sequence, as shown in FIG. 4, which can then be amplified. Alternatively, the insert section can contain an insignificant amount of target DNA 51 (such as when primer dimers occur or overly frequent priming occurs), such an embodiment is shown in FIG. 5. In some embodiments, the insignificant amount of DNA 51 will be no DNA, as such, the insert section is only 50 connected to 52. In other embodiments, a small amount of the target nucleic acid sequence is included 51. In some embodiments, the insert section for the double-extended loopable primer to be amplified is between 200 bp and 10 kb nucleic acids in length. In some embodiments, the insert section for the double-extended loopable primer to be amplified is between 100 bp and 20 kb nucleotides in length.

As will be appreciated by one of skill in the art, in some embodiments, the insert section 9 can be looped, such as by the hybridization of the universal region and the universal region complement in a double-extended primer 8, as shown in FIG. 4, (e.g. the loop formed by the self-hybridization of the double-extended linear primer). However, in other embodiments, the insert section is not actually looped during various amplification steps (although they will be looped for the shorter insert sections, such as primer dimers, that are not to be amplified). As described in more detail below, even when not part of a looped structure, the length of the insert section or target section can still influence the amplification of the section. For example, shorter length insert sections will result in closer to zero order reaction kinetics between the universal region and its complement, while longer insert sections will increase the distance between the universal region and its complement, resulting in slower reaction kinetics. Thus, double extended loopable primers need not be looped in order to allow for selective amplification of longer insert sections over shorter insert sections. As will be appreciated by one of skill in the art, one can characterize the insert section as including some of the loopable primer sequence. Unless otherwise stated, "insert section" will include the region to which the loopable primer initially binds. Thus, a double extended loopable primer that is only a primer dimer, even if it includes nothing more than the random region of the loopable primer, can still be characterized as "having" some part of an insert section that is shorter than another double extended loopable primer. That is, an "insert section" does not have to include any target (or foreign) nucleic acid sequence and can simply be one or two random regions from the loopable primers.

The "capture stem" or "insert stem" denotes the section of the double-extended loopable primer that is self-hybridized. As will be appreciated by one of skill in the art, when the double extended loopable primer is simply a primer dimer, without any additional target nucleic acid sequence, the insert section will comprise the original loopable primer sequences. As the structure can still be looped, there can still be unpaired nucleotides within the loop (although there need not be). Such primer dimer formations can be characterized as having "no foreign insert section", as they contain no additional sequence, apart from the starting primers; however, as they will still include the 3' target specific regions, there can still be a sequence within the insert section, even though none of it is foreign.

The term "insert amplification primer" refers to a primer that can be used to amplify an insert section. Generally, these primers are complementary to some section of the target nucleic acid sequence that is within the double-extended loopable primer. In some embodiments, the insert amplification primers are specific primers with known or knowable sequences. Thus, in some embodiments, numerous insert amplification primers will be employed as the specific sequence that has been amplified may not be known. In some embodiments, two or more insert amplification primers are used to amplify the insert sections. In some embodiments, each insert amplification primer (or paired set thereof) will be combined with the double-extended loopable primer in a separate reaction chamber (thus the amplified double-extended loopable primer will be divided among numerous reaction chambers). In other embodiments, the numerous insert amplification primers and the amplification reaction are performed in a single reaction chamber or are combined in some manner. In some embodiments, the insert amplification primers are degenerate primers. In some embodiments, the insert amplification primers are relatively short to allow for ease of amplification. In some embodiments, the insert amplification primers include universal bases.

The term "intramolecular hybridization" refers to an event or state in which a nucleic acid strand is hybridized to itself. This can include both the hybridization event that is present in the looped primer, as well as the hybridization event that occurs between the two ends of a double extended looped primer via the universal region and the universal region complement.

The terms "self-hybridizing" or "self-hybridized" refer to an event or state in which a portion of a nucleic acid strand is hybridized to another portion of itself. While the loopable primers are self-hybridizing, in general, the term is reserved for the effective hybridization of the universal region of the loopable primer to at least a portion of the universal region complement (which can be within a loopable primer complement) in a double extended loopable primer, e.g., as shown in FIG. 4 configuration 8. For example the universal region can be hybridized to the universal region complement.

The term "large enough to allow amplification" in reference to the insert section (or capture section) denotes that, relative to other species of sequences in the reaction mixture, the larger size of the insert section of the described species allows for greater or more efficient amplification. If an insert section has a "significant portion of target DNA" it will be large enough to allow amplification. In some embodiments, the insert section is between 200 bp and 10 kb or more nucleic acids in length. In some embodiments, the relative prevention of amplification is between a primer dimer (which comprises only the sequence of the loopable primer, e.g., a primer dimer) and a double extended loopable primer that includes at least one nucleotide in addition to the loopable primer.

The term "short enough to reduce the likelihood that amplification will occur" in reference to the insert section denotes that, relative to other species of sequences in the reaction mixture, the smaller size of the insert of the described species results in less and/or less efficient amplification compared to another species in the reaction mixture. If an insert has "an insignificant amount of target DNA" it is small enough to prevent or reduce the likelihood of amplification of DNA within the insert. In some embodiments, an insert that is short enough to reduce the likelihood that amplification will occur is between 1 and 200 nucleotides in length. As will be appreciated by one of skill in the art, as the loopable primer and primer complement can include a 3' target specific region some amount of a target nucleic acid sequence can be present, even in situations where simple primer dimerization has occurred. In some embodiments, these two terms are defined relative to one another. As will be appreciated by one of skill in the art in light of the present disclosure, in some embodiments, the size of the insert section (or insert section) is being used to preferentially reduce the amplification of smaller amplified regions of the target nucleic acid sequence compared to larger target nucleic acid sequences. Thus, in some embodiments, the "prevention" or "reduction" of the amplification of a first double-extended loopable primer over a second double-extended loopable primer results from the fact that the first has a shorter insert section compared to the second. In some embodiments, any difference in size of the insert section can result in the desired "reduction" or selective amplification, for example, the first double extended can be 99-90, 90-80, 80-70, 70-60, 60-50, 50-40, 40-30, 30-20, 20-10, 10-5, 5-1, 1-0.1, 0.1-0.001% or less the size of the insert section in the second double-extended loopable primer. In some embodiments, the prevention or reduction is specific to the prevention of the amplification of primer dimers. In some embodiments, the relative prevention is between designated larger and smaller inserts. In some embodiments, the relative prevention or reduction in likelihood is in comparison to the same sequence as the insert sequence, except that the sequence is not looped (e.g., same insert sections sequence, but no or insignificant amounts of the stem forming region).

As will be appreciated by one of skill in the art, in embodiments in which one is amplifying within a self-hybridized structure, at large enough lengths, the amplification in the insert section does not change significantly upon increasing the length of the nucleic acid sequence in the insert section. However, these sequences can still be preferentially amplified over double-extended loopable primers having shorter lengths of insert sections. As noted below, in some embodiments, insert sections of at least 100 bp are generally used in order to have amplification in the loop. In embodiments in which SNP genotyping and gene dosage RT-PCR are employed, the length of the loops can be 100 bp or longer, in order to allow spacing for two primers and probes (e.g., TAQMAN™ probes). For some embodiments, such as capillary electrophoresis for sequencing applications, the insert sections can be 500 bp or longer. Insert sections of at least 500 bp can result in very efficient amplification in the loop. If longer loops are desired, the annealing time and/or extension time can be increased during PCR. In embodiments in which a self-hybridized structure is not formed for the longer double-extended loopable primer, then there need be no minimal size, as long as it is longer than the other double-extended loopable primer that the long double extended loopable primer is to be amplified over.

As used herein, the term "identifying portion" refers to a moiety or moieties that can be used to identify a particular loopable primer species, and can refer to a variety of distinguishable moieties including zipcodes, a known number of nucleobases, and combinations thereof. In some embodiments, an identifying portion, or an identifying portion complement, can hybridize to a detector probe, thereby allowing detection of a target nucleic acid sequence in a decoding reaction. The terms "identifying portion complement" typically refers to at least one oligonucleotide that comprises at least one sequence of nucleobases that are at least substantially complementary to and hybridize with their corresponding identifying portion. In some embodiments, identifying portion complements serve as capture moieties for attaching at least one identifier portion and target nucleic acid sequence to at least one substrate; serve as "pull-out" sequences for bulk separation procedures; or both as capture moieties and as pull-out sequences (see for example O'Neil, et al., U.S. Pat. Nos. 6,638,760, 6,514,699, 6,146,511, and 6,124,092).

Typically, identifying portions and their corresponding identifying portion complements are selected to minimize: internal, self-hybridization; cross-hybridization with different identifying portion species, nucleotide sequences in a reaction composition, including but not limited to gDNA, different species of identifying portion complements, or target-specific portions of probes, and the like; but should be amenable to *facile* hybridization between the identifying portion and its corresponding identifying portion complement. Identifying portion sequences and identifying portion complement sequences can be selected by any suitable method, for example but not limited to, computer algorithms such as described in PCT Publication Nos. WO 96/12014 and WO 96/41011 and in European Publication No. EP 799,897; and the algorithm and parameters of SantaLucia (Proc. Natl. Acad. Sci. 95:1460-65 (1998)). Descriptions of identifying portions can be found in, among other places, U.S. Pat. No. 6,309,829 (referred to as "tag segment" therein); U.S. Pat. No. 6,451,525 (referred to as "tag segment" therein); U.S. Pat. No. 6,309,829 (referred to as "tag segment" therein); U.S. Pat. No. 5,981,176 (referred to as "grid oligonucleotides" therein); U.S. Pat. No. 5,935,793 (referred to as "identifier tags" therein); and PCT Publication No. WO 01/92579 (referred to as "addressable support-specific sequences" therein).

In some embodiments, the stem and/or loop of the loopable primer can comprise an identifying portion, and the detector probe can hybridize to the corresponding identifying portion. In some embodiments, the detector probe can hybridize to both the identifying portion as well as sequence corresponding to the target nucleic acid sequence. In some embodiments, at least two identifying portion: identifying portion complement duplexes have melting temperatures that fall within a $\Delta T_m$ range ($T_{max}-T_{min}$) of no more than 10° C. of each other. In some embodiments, at least two identifying portion-identifying portion complement duplexes have melting temperatures that fall within a $\Delta T_m$ range of 5° C. or less of each other. In some embodiments, at least two identifying portion-identifying portion complement duplexes have melting temperatures that fall within a $\Delta T_m$ range of 2° C. or less of each other.

In some embodiments, at least one identifying portion or at least one identifying portion complement is used to separate the element to which it is bound from at least one other component of a ligation reaction composition, a digestion reaction composition, an amplified ligation reaction composition, or the like. In some embodiments, identifying portions are used to attach at least one ligation product, at least one ligation product surrogate, or combinations thereof, to at least one substrate. In some embodiments, at least one ligation product, at least one ligation product surrogate, or combinations thereof, comprise the same identifying portion. Examples of separation approaches include but are not limited to, separating a multiplicity of different element-identifying portion species using the same identifying portion complement, tethering a multiplicity of different element-identifying portion species to a substrate comprising the same identifying portion complement, or both. In some embodiments, at least one identifying portion complement comprises at least one label, at least one mobility modifier, at least one label binding portion, or combinations thereof. In some embodiments, at least one identifying portion complement is annealed to at least one corresponding identifying portion and, subsequently, at least part of that identifying portion complement is released and detected, see for example Published P.C.T. Application WO04/4634 to Rosenblum et al., and Published P.C.T. Application WO01/92579 to Wenz et al.

As will be appreciated by one of skill in the art, while the presently disclosed looped primers can include an identifying portion, it need not be included and is not included in some embodiments. In some embodiments, the loopable primer includes an identifying portion as well as the non-complementary region. Is some embodiments, the identifying portion is not the same as the noncomplementary region. In some embodiments, an identifying portion is not included in a loopable primer.

As used herein, the term "extension reaction" refers to an elongation reaction in which the 3' target specific portion of a loopable primer is extended to form an extension reaction product comprising a strand complementary to a target nucleic acid sequence. In some embodiments, the target nucleic acid sequence is a gDNA molecule or fragment thereof. In some embodiments, the target nucleic acid sequence is a short DNA molecule and the extension reaction comprises a polymerase and results in the synthesis of a 2.sup.nd strand of DNA. In some embodiments, the consolidation of the extension reaction and a subsequent amplification reaction is further contemplated by the present teachings.

As used herein, the term "primer portion" refers to a region of a polynucleotide sequence that can serve directly, or by virtue of its complement, as the template upon which a primer can anneal for any of a variety of primer nucleotide extension reactions known in the art (for example, PCR). It will be appreciated by those of skill in the art that when two primer portions are present on a single polynucleotide, the orientation of the two primer portions is generally different. For example, one PCR primer can directly hybridize to a first primer portion, while another PCR primer can hybridize to the complement of the second primer portion. In some embodiments, "universal" primers and primer portions as used herein are generally chosen to be as unique as possible given the particular assays and sequences involved to ensure specificity of the assay. However, as will be appreciated by one of skill in the art, when a noncomplementary region is employed, the need for uniqueness with regard to the universal region is greatly diminished if not removed completely.

Figure 7:
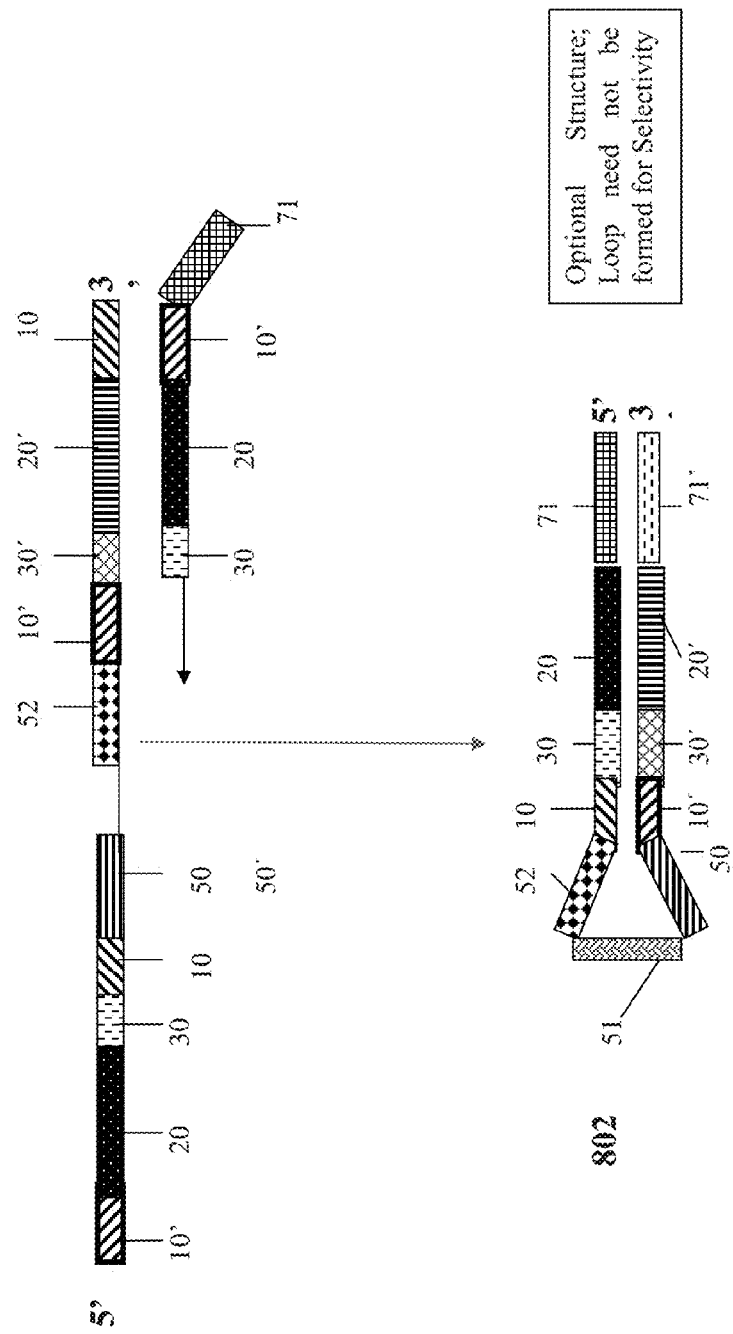
FIG. 7 is a depiction of some embodiments in which various double-extended loopable primers are self-hybridized.

The term "tail region" of a primer denotes a section at the 5' end of a primer sequence. In some embodiments this section can hybridize to part of a target sequence or priming site (e.g. such that the entire primer is hybridized to a target sequence or priming site). In some embodiments, the tail region has a sequence that is not complementary to the nucleic acid sequence that the remaining portion of the primer has hybridized to (e.g., the 5' end is not hybridized to a priming site while the rest of the primer can hybridize). In some embodiments, primers having different tail regions are used so as to allow for a sequence difference to be made at each end of the nucleic acid sequence (e.g. as shown in FIG. 7). Such a tail region can be denoted as a "noncomplementary tail region" or a second tail region, wherein the second tail region is different from the first. In some embodiments, the tail portion can include a zip-code, which can allow for the identification or tracking of the molecule associated with the zip-code. In some embodiments, the tail portion of the forward primer is between 5-8 nucleotides long. As will be appreciated by one of skill in the art, the length of the tail can determine the stability of the stem loop. If primer dimers are not a significant problem, the tail can be, for example, as large as a 20-mer to allow for the incorporation of forward and reverse primers for sequencing reactions that require two different primers. In some embodiments, one can reduce potential primer-dimer formation from carry over random primers by using tails that are less than 5-8 nucleotides in length. In some embodiments, a noncomplementary tail region is not used.

In some embodiments, the tail portion of the forward primer is 6 nucleotides long. Those in the art will appreciate that forward primer tail portion lengths shorter than 5 nucleotides and longer than 8 nucleotides can be identified in the course of routine methodology and without undue experimentation, and that such shorter and longer forward primer tail portion lengths are contemplated by the present teachings.

The term "upstream" as used herein takes on its customary meaning in molecular biology, and refers to the location of a region of a polynucleotide that is on the 5' side of a "downstream" region. Correspondingly, the term "downstream" refers to the location of a region of a polynucleotide that is on the 3' side of an "upstream" region.

As used herein, the term "hybridization" refers to the complementary base-pairing interaction of one nucleic acid with another nucleic acid that results in formation of a duplex, triplex, or other higher-ordered structure, and is used herein interchangeably with "annealing." Typically, the primary interaction is base specific, e.g., A/T and G/C, by Watson/Crick and Hoogsteen-type hydrogen bonding. Base-stacking and hydrophobic interactions can also contribute to duplex stability. Conditions for hybridizing detector probes and primers to complementary and substantially complementary target sequences are well known, e.g., as described in Nucleic Acid Hybridization, A Practical Approach, B. Hames and S. Higgins, eds., IRL Press, Washington, D.C. (1985) and J. Wetmur and N. Davidson, Mol. Biol. 31:349 et seq. (1968). In general, whether such annealing takes place is influenced by, among other things, the length of the polynucleotides and the complementarity, the pH, the temperature, the presence of mono- and divalent cations, the proportion of G and C nucleotides in the hybridizing region, the viscosity of the medium, and the presence of denaturants. Such variables influence the time required for hybridization. Thus, the preferred annealing conditions will depend upon the particular application. Such conditions, however, can be routinely determined by the person of ordinary skill in the art without undue experimentation. It will be appreciated that complementarity need not be perfect; there can be a small number of base pair mismatches that will minimally interfere with hybridization between the target sequence and the single stranded nucleic acids of the present teachings. However, if the number of base pair mismatches is so great that no hybridization can occur under minimally stringent conditions then the sequence is generally not a complementary target sequence. Thus, complementarity herein is meant that the probes or primers are sufficiently complementary to the target sequence to hybridize under the selected reaction conditions to achieve the ends of the present teachings. Something is "configured to hybridize" when its sequence (e.g. structure) allows hybridization through base specific, (e.g., A/T and G/C, by Watson/Crick and Hoogsteen-type hydrogen bonding.

As used herein, the term "amplifying" refers to any method by which at least a part of a target nucleic acid sequence, target nucleic acid sequence surrogate, or combinations thereof, is reproduced, typically in a template-dependent manner, including without limitation, a broad range of techniques for amplifying nucleic acid sequences, either linearly or exponentially. Exemplary means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA) and the like, including multiplex versions or combinations thereof, for example but not limited to, OLA/PCR, PCR/OLA, LDR/PCR, PCR/PCR/LDR, PCR/LDR, LCR/PCR, PCR/LCR (also known as combined chain reaction-CCR), and the like. Descriptions of such techniques can be found in, among other places, Sambrook et al. Molecular Cloning, 3.sup.rd Edition; Ausbel et al.; PCR Primer: A Laboratory Manual, Diffenbach, Ed., Cold Spring Harbor Press (1995); The Electronic Protocol Book, Chang Bioscience (2002), Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. No. 6,027,998; U.S. Pat. No. 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf Dis. 2:18-(2002); Lage et al., Genome Res. 2003 February; 13(2):294-307, and Landegren et al., Science 241:1077-80 (1988), Demidov, V., Expert Rev Mol. Diagn. 2002 November; 2(6):542-8., Cook et al., J Microbiol Methods. 2003 May; 53(2):165-74, Schweitzer et al., Curr Opin Biotechnol. 2001 February; 12(1):21-7, U.S. Pat. No. 5,830,711, U.S. Pat. No. 6,027,889, U.S. Pat. No. 5,686,243, Published P.C.T. Application WO0056927A3, and Published P.C.T. Application WO9803673A1. In some embodiments, newly-formed nucleic acid duplexes are not initially denatured, but are used in their double-stranded form in one or more subsequent steps. An extension reaction is an amplifying technique that comprises elongating a loopable primer that is annealed to a template in the 5' to 3' direction using an amplifying means such as a polymerase and/or reverse transcriptase. According to some embodiments, with appropriate buffers, salts, pH, temperature, and nucleotide triphosphates, including analogs thereof, i.e., under appropriate conditions, a polymerase incorporates nucleotides complementary to the template strand starting at the 3'-end of an annealed loopable primer, to generate a complementary strand. In some embodiments, the polymerase used for extension lacks or substantially lacks 5' exonuclease activity. In some embodiments of the present teachings, unconventional nucleotide bases can be introduced into the amplification reaction products and the products treated by enzymatic (e.g., glycosylases) and/or physical-chemical means in order to render the product incapable of acting as a template for subsequent amplifications. In some embodiments, uracil can be included as a nucleobase in the reaction mixture, thereby allowing for subsequent reactions to decontaminate carryover of previous uracil-containing products by the use of uracil-N-glycosylase (see for example Published P.C.T. Application WO9201814A2). In some embodiments of the present teachings, any of a variety of techniques can be employed prior to amplification in order to facilitate amplification success, as described for example in Radstrom et al., Mol. Biotechnol. 2004 February; 26(2):13346. In some embodiments, amplification can be achieved in a self-contained integrated approach comprising sample preparation and detection, as described for example in U.S. Pat. Nos. 6,153,425 and 6,649,378. Reversibly modified enzymes, for example but not limited to those described in U.S. Pat. No. 5,773,258, are also within the scope of the disclosed teachings. The present teachings also contemplate various uracil-based decontamination strategies, wherein for example uracil can be incorporated into an amplification reaction, and subsequent carry-over products removed with various glycosylase treatments (see for example U.S. Pat. No. 5,536,649, and U.S. Provisional Application 60/584,682 to Andersen et al.). Those in the art will understand that any protein with the desired enzymatic activity can be used in the disclosed methods and kits. Descriptions of DNA polymerases, including reverse transcriptases, uracil N-glycosylase, and the like, can be found in, among other places, Twyman, Advanced Molecular Biology, BIOS Scientific Publishers, 1999; Enzyme Resource Guide, rev. 092298, Promega, 1998; Sambrook and Russell; Sambrook et al.; Lehninger; PCR: The Basics; and Ausbel et al.

As used herein, the term "detector probe" refers to a molecule used in an amplification reaction, typically for quantitative or real-time PCR analysis, as well as end-point analysis. Such detector probes can be used to monitor the amplification of the target nucleic acid sequence. In some embodiments, detector probes present in an amplification reaction are suitable for monitoring the amount of amplicon(s) produced as a function of time. Such detector probes include, but are not limited to, the 5'-exonuclease assay (TAQMAN™ probes described herein (see also U.S. Pat. No. 5,538,848) various stem-loop molecular beacons (see e.g., U.S. Pat. Nos. 6,103,476 and 5,925,517 and Tyagi and Kramer, 1996, Nature Biotechnology 14:303-308), stemless or linear beacons (see, e.g., WO 99/21881), PNA Molecular Beacons™ (see, e.g., U.S. Pat. Nos. 6,355,421 and 6,593,091), linear PNA beacons (see, e.g., Kubista et al., 2001, SPIE 4264:53-58), non-FRET probes (see, e.g., U.S. Pat. No. 6,150,097), Sunrise™/Amplifluor™ probes (U.S. Pat. No. 6,548,250), stem-loop and duplex Scorpion probes (Solinas et al., 2001, Nucleic Acids Research 29:E96 and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596, 490), peptide nucleic acid (PNA) light-up probes, self-assembled nanoparticle probes, and ferrocene-modified probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem. Res. Toxicol. 15:118-126; and Yu et al., 2001, J. Am. Chem. Soc 14:11155-11161. Detector probes can also comprise quenchers, including without limitation black hole quenchers (Biosearch), Iowa Black (IDT), QSY quencher (Molecular Probes), and Dabsyl and Dabcel sulfonate/carboxylate Quenchers (Epoch). Detector probes can also comprise two probes, wherein for example a fluor is on one probe, and a quencher is on the other probe, wherein hybridization of the two probes together on a target quenches the signal, or wherein hybridization on the target alters the signal signature via a change in fluorescence. Detector probes can also comprise sulfonate derivatives of fluorescenin dyes with $SO_3$ instead of the carboxylate group, phosphoramidite forms of fluorescein, phosphoramidite forms of CY 5 (commercially available for example from Amersham). In some embodiments, interchelating labels are used such as ethidium bromide, SYBR™ Green I (Molecular Probes), and PicoGreen™ (Molecular Probes), thereby allowing visualization in real-time, or end point, of an amplification product in the absence of a detector probe. In some embodiments, real-time visualization can comprise both an intercalating detector probe and a sequence-based detector probe can be employed. In some embodiments, the detector probe is at least partially quenched when not hybridized to a complementary sequence in the amplification reaction, and is at least partially unquenched when hybridized to a complementary sequence in the amplification reaction. In some embodiments, the detector probes of the present teachings have a Tm of 63-69° C., though it will be appreciated that guided by the present teachings routine experimentation can result in detector probes with other Tms. In some embodiments, probes can further comprise various modifications such as a minor groove binder (see for example U.S. Pat. No. 6,486,308) to further provide desirable thermodynamic characteristics. In some embodiments, detector probes can correspond to identifying portions or identifying portion complements.

The term "corresponding" as used herein refers to a specific relationship between the elements to which the term refers. Some non-limiting examples of corresponding include: a loopable primer can correspond with a target nucleic acid sequence, and vice versa. A forward primer can correspond with a target nucleic acid sequence, and vice versa. In some cases, the corresponding elements can be complementary. In some cases, the corresponding elements are not complementary to each other, but one element can be complementary to the complement of another element.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, the term "reaction vessel" or "reaction chamber" generally refers to any container in which a reaction can occur in accordance with the present teachings. In some embodiments, a reaction vessel can be an eppendorf tube or other container of the sort in common use in modern molecular biology laboratories. In some embodiments, a reaction vessel can be a well in microtitre plate, a spot on a glass slide, or a well in an Applied Biosystems TaqMan Low Density Array for gene expression (formerly MicroCard™). A plurality of reaction vessels can reside on the same support. In some embodiments, lab-on-a-chip like devices, available for example from Caliper and Fluidgm, can provide for reaction vessels. In some embodiments, various microfluidic approaches as described in U.S. Provisional Application 60/545,674 to Wenz et al., can be employed. It will be recognized that a variety of reaction vessels are available in the art and within the scope of the present teachings.

As used herein, the term "detection" refers to a way of determining the presence and/or quantity and/or identity of a target nucleic acid sequence. In some embodiments, the sequence to be detected is known. Thus, in some embodiments, detection occurs by determining if the target nucleic acid sequence comprises or consists of a known nucleic acid sequence, gene, etc. In some embodiments, the sequence to be detected is not known prior to the experiment. In such embodiments, the target nucleic acid sequence is amplified and sequenced. The sequencing of the target nucleic acid can be characterized as "detecting" the target nucleic acid. The target nucleic acid sequence to be sequenced can be known or unknown prior to its sequencing. Thus, in some embodiments, a target nucleic acid is sequenced to determine if a specific sequence or gene is present in a sample, and/or determine what specific variant is present. In some embodiments, a target nucleic acid is sequenced to determine the sequences of the genes or nucleic acid sequences themselves (e.g., the sequence and/or identity of the target nucleic acid sequence is not known prior to sequencing).

In some embodiments employing a donor moiety and signal moiety, one can use certain energy-transfer fluorescent dyes for detection. Certain nonlimiting exemplary pairs of donors (donor moieties) and acceptors (signal moieties) are illustrated, e.g., in U.S. Pat. Nos. 5,863,727; 5,800,996; and 5,945,526. Use of some combinations of a donor and an acceptor have been called FRET (Fluorescent Resonance Energy Transfer). In some embodiments, fluorophores that can be used as signaling probes include, but are not limited to, rhodamine, cyanine 3 (Cy 3), cyanine 5 (Cy 5), fluorescein, VIC, LIZ, TAMRA. (carboxytetramethylrhodamine, succinimidyl ester), 5-FAM. (5-carboxyfluorescein), 6-FAM (6-carboxyfluorescein), and Texas Red (Molecular Probes). (VIC, LIZ, TAMRA, 5-FAM, and 6-FAM all available from Applied Biosystems, Foster City, Calif.).

In some embodiments, the amount of detector probe that gives a fluorescent signal in response to an excited light typically relates to the amount of nucleic acid produced in the amplification reaction. Thus, in some embodiments, the amount of fluorescent signal is related to the amount of product created in the amplification reaction. In such embodiments, one can therefore measure the amount of amplification product by measuring the intensity of the fluorescent signal from the fluorescent indicator. According to some embodiments, one can employ an internal standard to quantify the amplification product indicated by the fluorescent signal. See, e.g., U.S. Pat. No. 5,736,333. Devices have been developed that can perform a thermal cycling reaction with compositions containing a fluorescent indicator, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670, and include, but are not limited to the ABI Prism™. 7700 Sequence Detection System (Applied Biosystems, Foster City, Calif.), the ABI GeneAmp™. 5700 Sequence Detection System (Applied Biosystems, Foster City, Calif.), the ABI GeneAmp™. 7300 Sequence Detection System (Applied Biosystems, Foster City, Calif.), and the ABI GeneAmp™. 7500 Sequence Detection System (Applied Biosystems). In some embodiments, each of these functions can be performed by separate devices. For example, if one employs a Q-beta replicase reaction for amplification, the reaction does not need to take place in a thermal cycler, but could include a light beam emitted at a specific wavelength, detection of the fluorescent signal, and calculation and display of the amount of amplification product. In some embodiments, combined thermal cycling and fluorescence detecting devices can be used for precise quantification of target nucleic acid sequences in samples. In some embodiments, fluorescent signals can be detected and displayed during and/or after one or more thermal cycles, thus permitting monitoring of amplification products as the reactions occur in "real time." In some embodiments, one can use the amount of amplification product and number of amplification cycles to calculate how much of the target nucleic acid sequence was in the sample prior to amplification.

In some embodiments, one can simply monitor the amount of amplification product after a predetermined number of cycles sufficient to indicate the presence of the target nucleic acid sequence in the sample. One skilled in the art can easily determine, for any given sample type, primer sequence, and reaction condition, how many cycles are sufficient to determine the presence of a given target nucleic acid sequence. As used herein, determining the presence of a target can comprise identifying it, as well as optionally quantifying it. In some embodiments, the amplification products can be scored as positive or negative as soon as a given number of cycles is complete. In some embodiments, the results can be transmitted electronically directly to a database and tabulated. Thus, in some embodiments, large numbers of samples can be processed and analyzed with less time and labor when such an instrument is used.

In some embodiments, different detector probes can distinguish between different target nucleic acid sequences. A non-limiting example of such a probe is a 5'-nuclease fluorescent probe, such as a TaqMan™ probe molecule, wherein a fluorescent molecule is attached to a fluorescence-quenching molecule through an oligonucleotide link element. In some embodiments, the oligonucleotide link element of the 5'-nuclease fluorescent probe binds to a specific sequence of an identifying portion or its complement. In some embodiments, different 5'-nuclease fluorescent probes, each fluorescing at different wavelengths, can distinguish between different amplification products within the same amplification reaction. For example, in some embodiments, one could use two different 5'-nuclease fluorescent probes that fluoresce at two different wavelengths ($WL_A$ and $WL_B$) and that are specific to two different stem regions of two different extension reaction products (A' and B', respectively). Amplification product A' is formed if target nucleic acid sequence A is in the sample, and amplification product B' is formed if target nucleic acid sequence B is in the sample. In some embodiments, amplification product A' and/or B' can form even if the appropriate target nucleic acid sequence is not in the sample, but such occurs to a measurably lesser extent than when the appropriate target nucleic acid sequence is in the sample. After amplification, one can determine which specific target nucleic acid sequences are present in the sample based on the wavelength of signal detected and their intensity. Thus, if an appropriate detectable signal value of only wavelength $WL_A$ is detected, one would know that the sample includes target nucleic acid sequence A, but not target nucleic acid sequence B. If an appropriate detectable signal value of both wavelengths $WL_A$ and $WL_B$ are detected, one would know that the sample includes both target nucleic acid sequence A and target nucleic acid sequence B.

In some embodiments, detection can occur through any of a variety of mobility dependent analytical techniques based on differential rates of migration between different analyte species. Exemplary mobility-dependent analysis techniques include electrophoresis, chromatography, mass spectroscopy, sedimentation, e.g., gradient centrifugation, field-flow fractionation, multi-stage extraction techniques, and the like. In some embodiments, mobility probes can be hybridized to amplification products, and the identity of the target nucleic acid sequence determined via a mobility dependent analysis technique of the eluted mobility probes, as described for example in Published P.C.T. Application WO04/46344 to Rosenblum et al., and WO01/92579 to Wenz et al. In some embodiments, detection can be achieved by various microarrays and related software such as the Applied Biosystems Array System with the Applied Biosystems 1700 Chemiluminescent Microarray Analyzer and other commercially available array systems available from Affymetrix, Agilent, Illumina, and Amersham Biosciences, among others (see also Gerry et al., J. Mol. Biol. 292:251-62, 1999; De Bellis et al., Minerva Biotec 14:247-52, 2002; and Stears et al., Nat. Med. 9:14045, including supplements, 2003). It will also be appreciated that detection can comprise reporter groups that are incorporated into the reaction products, either as part of labeled primers or due to the incorporation of labeled dNTPs during an amplification, or attached to reaction products, for example but not limited to, via hybridization tag complements comprising reporter groups or via linker arms that are integral or attached to reaction products. Detection of unlabeled reaction products, for example using mass spectrometry, is also within the scope of the current teachings.

In some embodiments, the term "universal region" as used herein refers to a region of an oligonucleotide primer that is designed to have no significant homology to any segment in the genome. However, as will be appreciated by one of skill in the art, given that the universal region can be included within the looped section of the loopable primer, the risk of nonspecific priming is greatly reduced, thereby removing this requirement for embodiments in which the universal region is within a loopable primer. Similarly, given that, in some embodiments, a noncomplementary region is included in the loopable primer, nonspecific priming can be further reduced. Thus, in some embodiments, the universal region is a region that allows for priming with a known primer. In some embodiments, this primer is common to at least one other nucleic acid sequences. In some embodiments, the "universal region" meets all the requirements for a normal oligonucleotide primer, such as lack of secondary structure, an appropriate Tm, and an appropriate GC content and can be between about 8 and 35 bases in length, between about 15 and 25 bases in length or between about 18 and 22 bases in length. However, as will be appreciated by one of skill in the art, the universal region, when part of the loopable primer, will be part of a larger structure that has secondary structure. Additionally, because the universal region will be part of a larger primer, the universal region need only function as part of the entire loopable primer. As such, in these embodiments, the universal region need only assist in priming, as described in detail below. In other embodiments, the universal region functions independently as a priming site. In some embodiments, the universal region is the same as the noncomplementary region or they share some of the same nucleic acid sequences. "Universal priming site" when used herein refers to a "universal region" of a primer that can function as a site to which universal primers anneal for priming of further cycles of DNA amplification. In some embodiments, the loopable primer includes a universal region. The term "universal primer" as used herein refers to a primer that includes only a "universal region".

The term "anneal" as used herein refer to the base-pairing interaction of one polynucleotide with another polynucleotide that results in the formation of a duplex or other higher-ordered structure. The primary interaction is base specific, i.e., A/T and G/C, by Watson/Crick and Hoogsteen-type hydrogen bonding.

The term "real-time analysis" refers to periodic monitoring during PCR. Certain systems such as the ABI 7700 and 7900HT Sequence Detection Systems (Applied Biosystems, Foster City, Calif.) conduct monitoring during each thermal cycle at a pre-determined or user-defined point. Real-time analysis of PCR with FRET probes measures fluorescent dye signal changes from cycle-to-cycle, preferably minus any internal control signals.

The term "5'-nuclease analysis" or "5'-nuclease assay" when used herein refers to "real-time analysis" for quantification of the amount of DNA amplified in a particular PCR reaction. TAQMAN™ analysis is an example of such "5'-nuclease analysis" (a commercially available PCR kit). "5'-nuclease analysis" involves the use of a fluorogenic oligonucleotide probe to which a reporter dye and a quencher dye are attached. During amplification of a nucleotide sequence using a forward and reverse primer, the probe anneals to the target of interest between the forward and reverse primer sites. During extension, the probe is cleaved by the 5'-nuclease activity of the DNA polymerase. As the cleavage separates the reporter dye from the quencher dye, the reporter dye's fluorescence increases which can be detected and quantitated. Real-time analysis of PCR with 5'-nuclease assay involves FRET probes that can be displayed by plotting the logarithmic change in detected fluorescence ($\Delta Rn$) versus the cycle number. The cycle within the PCR protocol at which the change in fluorescence ($\Delta Rn$) rises above a threshold value is denoted as $C_T$. The $C_T$ cycle is approximately the cycle at which amplification of target becomes exponential. A relatively low $C_T$ value indicates efficient detection of amplicon. The threshold cycle is highly correlated to the amount of copy number, or amount of target nucleic acid sequence present in the sample, as well as the efficiency of amplification. The effects of primer constitution, e.g. length, sequence, mismatches, analogs, can be conveniently screened and quantitated by measurement of $C_T$ values during real-time analysis of PCR. In some embodiments, the sequences within the insert sections can be detected and/or amplified via a TAQMAN™ assay or similar assay.

"Polymerase chain reaction" or "PCR" as used herein, refers to a method in the art for amplification of a nucleic acid. The method can involve introducing a molar excess of two or more extendable oligonucleotide primers to a reaction mixture comprising the desired target sequence(s), where the primers hybridize to opposite strands of the double stranded target sequence. The reaction mixture is subjected to a program of thermal cycling in the presence of a DNA polymerase, resulting in the amplification of the desired target sequence flanked by the oligonucleotide primers. The oligonucleotide primers prime multiple sequential rounds of DNA synthesis, each round of synthesis is typically separated by a melting and re-annealing step. Methods for a wide variety of PCR applications are widely known in the art, and are described in many sources, for example, Ausubel et al. (eds.), Current Protocols in Molecular Biology, Section 15, John Wiley & Sons, Inc., New York (1994).

"In silico PCR" when used herein refers to a computer-conducted method for predicting the size and probability of amplification of a nucleotide sequence using a particular set of primers. The method involves searching a DNA database for exact matches to the primer sequences and further for sequences having the correct order, orientation, and spacing to allow priming of amplification of a nucleotide sequence of a predicted size.

"Tm" as used herein, refers to the melting temperature (temperature at which 50% of the oligonucleotide is a duplex) of the oligonucleotide calculated using the nearest-neighbor thermodynamic values of Breslauer et al. (Proc. Natl. Acad. Sci. USA 83:3746 3750, 1986) for DNA and Freier et al. (Proc. Natl. Acad. Sci. USA 83:9373 9377, 1986) for RNA.

As will be appreciated by one of skill in the art, the above definitions occasionally describe various embodiments that can also be used, in some embodiments, with the variously defined parts or steps. Unless indicated, these various embodiments are not required or part of the actual definitions and have been included for additional general context and for further description of the various contemplated embodiments.

Aspects of the present teachings can be further understood in light of the following description and examples, which should not be construed as limiting the scope of the present teachings in any way.

Loopable Primers and Uses Thereof

There are numerous strategies for nucleic acid amplification involving the use of random or degenerate primers. These primers can be especially useful in the amplification of unknown sequences, such as in whole genome amplification. To date, many of the techniques have drawbacks, including issues such as primer-dimer formation or the accumulation of other relatively short fragment artifacts that dominate PCR or other amplification products.

In some embodiments, some or all of the above issue(s) can be addressed by using loopable primers to prime the target nucleic acid. In some embodiments, these loopable primers include a random or degenerate priming sequence (or more generally 3' target specific regions), a universal region within the looped section, and, optionally, a non-complementary region and have a reduced likelihood of forming primer-dimers and/or resulting in other nonspecific priming events.

FIG. 1A depicts one embodiment of a loopable primer 6. The loopable primer can include a 3' target specific region 50, a first loop-forming region 10, an optional noncomplementary region 30, a second loop forming-region 10', and a universal region (also called a universal priming region) 20.

As described in more detail below, the noncomplementary region 30 can have various advantages in various embodiments. For example, by selecting a noncomplementary region that is relatively rare in the middle of gDNA (such as a poly T sequence), one can reduce the likelihood that spurious internal priming will occur in various amplification steps. Additionally, when various universal regions are employed, the presence of the noncomplementary region (which can be the same across all of the loopable primers) can reduce the likelihood that primer-dimers will form.

As described in detail below, and outlined in FIG. 1B, in some embodiments, the loopable primer can be used to initiate priming as desired (e.g. via a random or degenerate priming region), while still including a universal and a noncomplementary region in the primer. Moreover, this can be achieved with a reduced risk of nonspecific or primer-dimer interactions occurring.

Figure 1B:
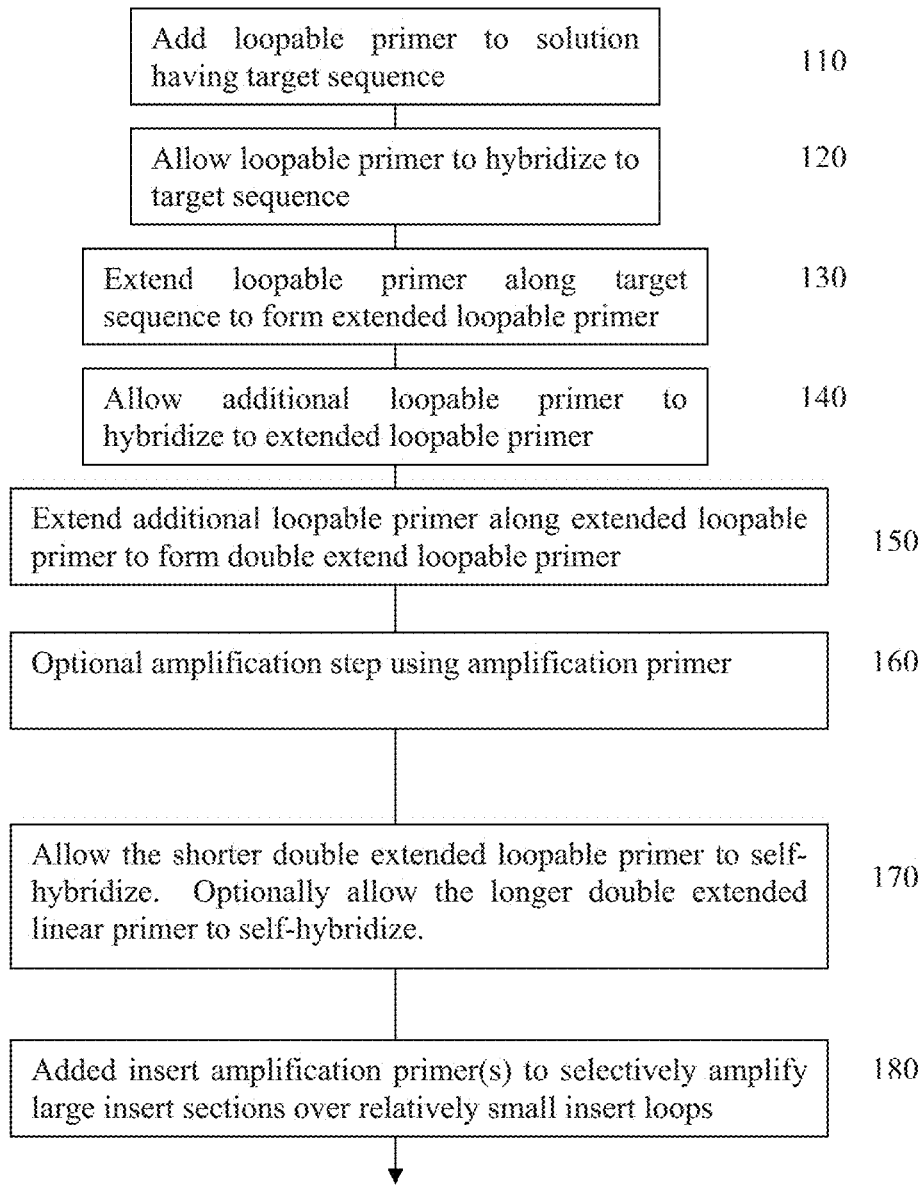
FIG. 1B is a flow chart depicting an embodiment of a method for selective amplification of a target.

In some embodiments, such as the one depicted in FIG. 1B, the use of the loopable primer to amplify sections of a target sequence allows one to place complementary sequences on either end of the amplified target nucleic acid sequence. As noted below, the addition of these complementary sequences allow for the size dependent amplification of the target nucleic acid sequences.

The first step depicted in FIG. 1B is the addition of a loopable primer (6 depicted in FIG. 1A) to a solution that includes the target nucleic acid sequence or sequences that are to be amplified 110 or in which a target is to be identified, if present. Conditions are selected such that the loopable primer hybridizes to the target sequence 120. The loopable primer is then extended along the target sequence to form an extended loopable primer 130. One can then allow the loopable primer (the same degenerate loopable primer, an identical loopable primer, or a different loopable primer, as long as the same universal region is present) to hybridize to the extended loopable primer 140. Then one can extend the additional loopable primer along the extended loopable primer to form a double-extended loopable primer 150. In various embodiments, the loopable primers can have identical sequences; can have identical sequences apart from the 3' target specific region; can have different sequences, apart from the noncomplementary region; or can have different sequences, as long as the noncomplementary regions will effectively reduce nonspecific priming of the loopable primer.

In some embodiments, some or all of steps 110-150 can be repeated as desired. In some embodiments, some or all of steps 110-150 can be repeated as desired prior to proceeding to step 160. Following the step 150, one can optionally amplify the double-extended loopable primer using an amplification primer 160. The amplification primer will have a sequence that will hybridize to a sequence that is complementary to the universal region on the primer (e.g. the amplification primer can have a sequence that is or is a part of the universal region) and optionally (if necessary) a sequence that will hybridize to the noncomplementary region. As will be appreciated by one of skill in the art, in some embodiments, only one of these regions will be present.

One can then allow the shorter double-extended loopable primer to self-hybridize 170. In some embodiments, one can allow both the short and the long double-extended loopable primers to self-hybridize. This self-hybridized population can then be used in the selective amplification of large insert sections over relatively small insert sections 180 (depicted in FIGS. 4 and 5). Thus, in some embodiments, the use of the loopable primer described above results in a self-hybridized population that allows for the selective amplification of larger sections of target nucleic acid sequences over smaller sections of target nucleic acid sequences contained within the self-hybridized structures. In some embodiments an initial reverse transcription step can be performed or a cleaning step can be included, for example as described in the following sections.

While the self-hybridized structure can be used to help select larger insert section (or insert sections) over smaller insert sections, the larger double extended loopable primer need not assume a looped configuration. For example, in some embodiments, the self-hybridized structure is only formed for the shorter insert sections. Thus, in some embodiments, selective amplification of longer insert sections over shorter insert sections (including primer dimers) occurs without the formation of a self-hybridized structure for the longer double extended loopable primer. Without intending to be limited by theory, it is understood that because a shorter insert sections will mean that there is less distance between the universal region and the universal region complement, that these short double extended loopable primers will self hybridize faster than double extended loopable primers with larger insert sections. Similarly, the larger double-extended loopable primers will have more distance between the loopable primer and its complement and thus it can take longer for the primer and its complement to self-hybridize. Thus, in some embodiments, it is the faster ability of the double extended loopable primers having shorter insert sections to self-hybridize, and thus take themselves out of a reaction, that allows for the selective amplification of the double extended loopable primers having the longer insert sections over the shorter (or no foreign) insert sections. Thus, in some embodiments, the longer or long insert section is not in a looped configuration during the selective amplification.

Figure 1C:
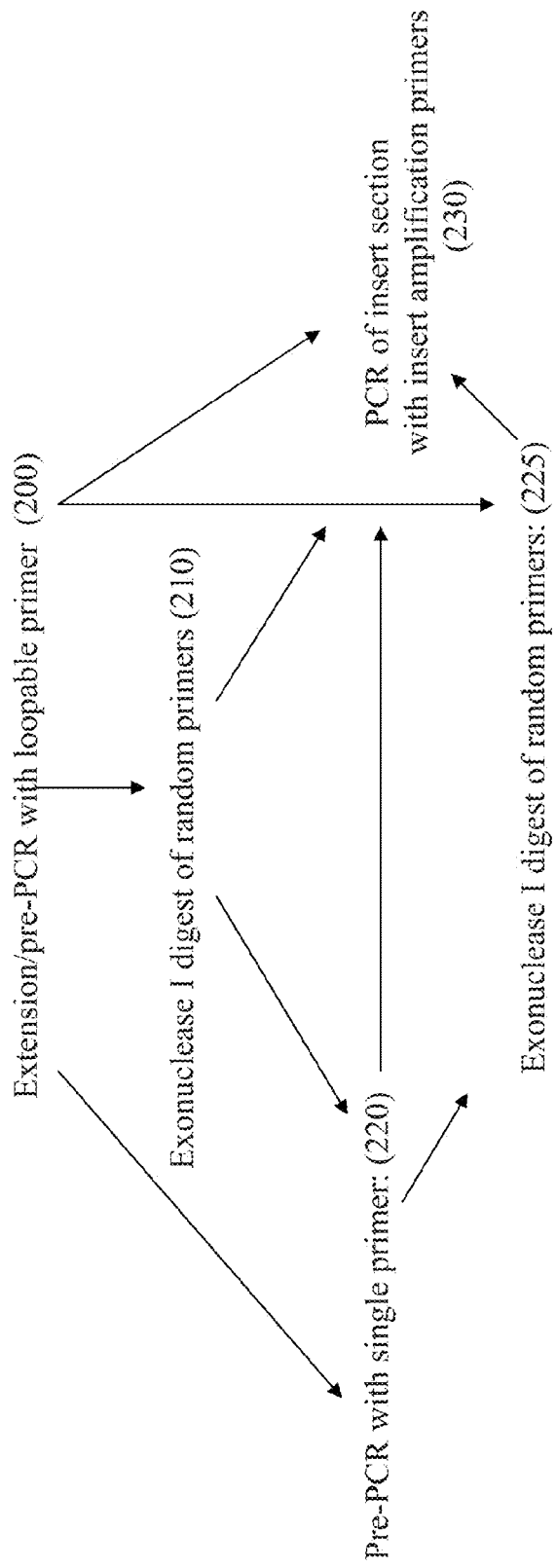
FIG. 1C is a flow chart depicting one embodiment of a method for selective amplification of a target while reducing the risk of undesirable priming events.

Additional embodiments of the method of using the loopable primers for the selective amplification of relatively larger target nucleic acid sequences (compared to shorter target nucleic acid sequences) are shown generally in FIG. 1C. The first step 200 can involve primer extension via the loopable primers described above (to form a double-extended loopable primer) which can be followed by step 210, a digestion of various random primers, such as with exonuclease I. In some embodiments, this is followed by a pre-PCR amplification step with a single amplification primer (step 220). Following this, a step is performed to amplify the insert section, depending upon the size of the target nucleic acid sequence within the insert section. This can be achieved with an insert amplification primer (step 230). As shown in FIG. 1C by the arrows, various steps can be included or removed for various embodiments. In some embodiments, the cleaning step 225 is not performed or is performed after the pre-PCR amplification 220. In some embodiments, multiple rounds of cleaning (e.g. exonuclease digestion) are employed. Specific embodiments involved in these methods are discussed in more detail in regard to FIGS. 2-7.

Figure 2:
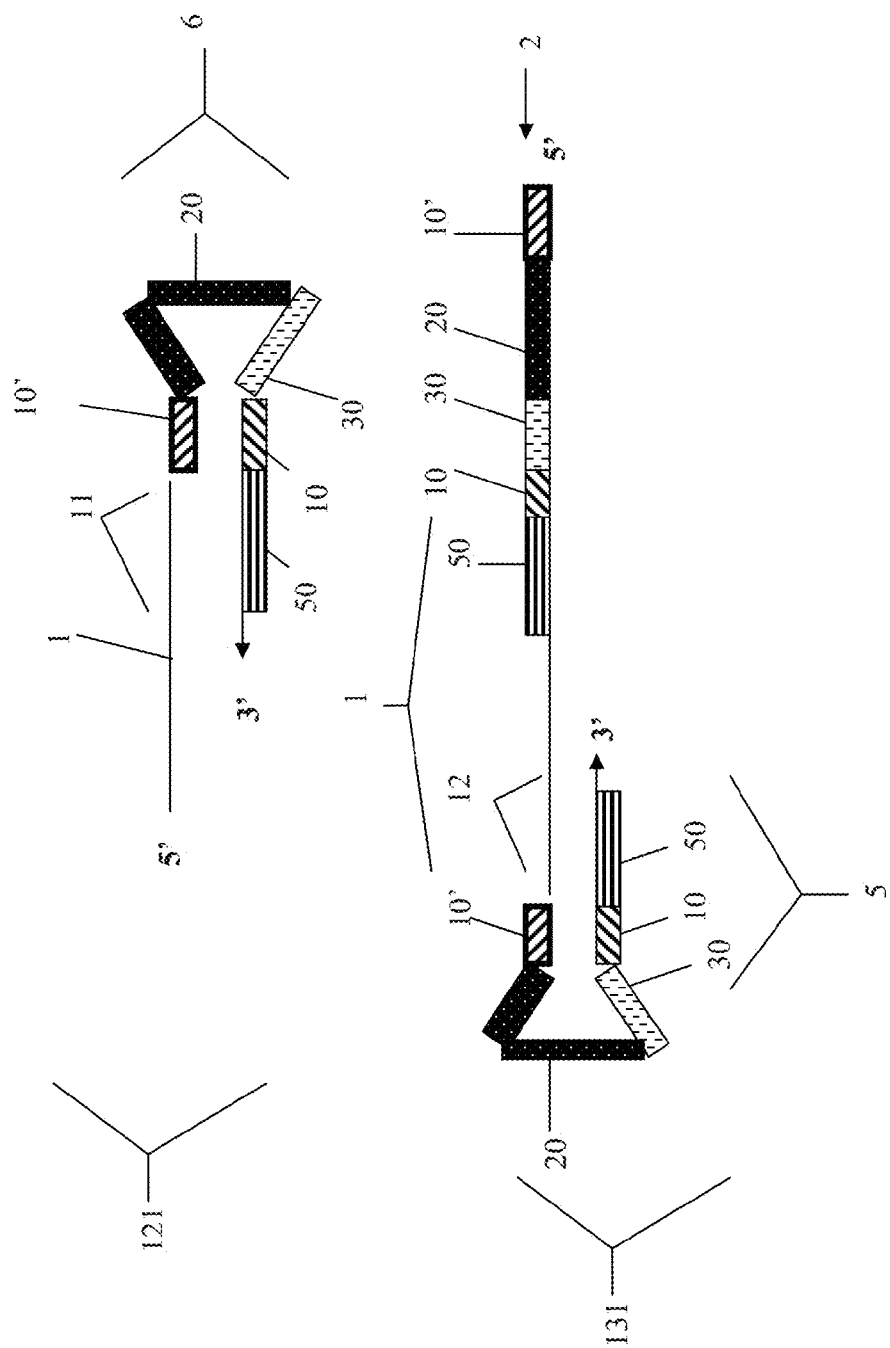
FIG. 2 is a depiction of one embodiment employing loopable primers.

In the top section of FIG. 2, the loopable primer 6 is shown hybridized at a first part 11 at a complementary portion of the target nucleic acid sequence 1 in a first arrangement 121. This results from a first step in which, the loopable primer 6 is allowed to anneal via the 3' target specific region 50 to the first part of the target nucleic acid sequence at a target binding site 11. Following the hybridization, the primer is extended along the target sequence in the 5' direction of the target sequence or in the 3' direction from the loopable primer (arrow). Following this extension, an additional loopable primer 5 (which can have the same sequence as the first loopable primer, a different sequence (but same universal region 20, and/or the same 3' target specific region 50 and/or noncomplementary region 30) hybridizes at a complementary portion of the extended loopable primer 2 at a second target binding site 12, as shown in FIG. 2, in a second arrangement 131. As above, the loopable primer 6 can include a 3' specific target region 50, a first loop-forming region 10, optionally a noncomplementary region 30, a universal region 20, and a second loop-forming region 10'. In some embodiments, the loopable primers 5 and 6are the same. In some embodiments, the loopable primers are the same, apart from their 3' target specific region 50.

In some embodiments, the 3' target specific region is a degenerate region; thus, identifier "50" can represent multiple or different sequences on different primers as it can be a degenerate sequence. For FIGS. 3-7, the 3' target specific region is depicted as identifier 50 and 52, (to provide additional clarity for some embodiments in which the 3' target specific region is degenerate), and thus the specific sequences of 50 and 52 are identified by different identifiers in these figures. However, both 50 and 52 are 3' target specific regions (and thus can be the same in some embodiments). In addition, the 3' target specific region identifier "50" can be used generically throughout a single figure (such as in FIG. 2), to denote different sequences, even though a single identifier is used (thus, both "50" and "52" need not be present to denote that a region is degenerate). One of skill in the art will readily appreciate how this and other sequences within these loopable primers 5 & 6 can be differed, if desired.

Following the hybridization of the loopable primer 6 to the extended loopable primer 2the loopable primer 6 is extended from its 3' direction to the 5' direction of the extended loopable primer. This extension results in a double-extended loopable primer 4 (FIG. 3). As noted above, the term "double-extended loopable primer" does not imply that the sequence functions as a primer but that it is formed from extending loopable primers.

The double-extended loopable primer can optionally be amplified at this point. This is shown in more detail in FIG. 3 in which an amplification primers 60 is used to amplify the double-extended loopable primer 4. In some embodiments, the first amplification primer includes, comprises, consists, or consists essentially of a universal region. In some embodiments, the first amplification primer includes a sequence that is the same as the noncomplementary region 30 of the first loopable primer, a sequence that is the same as the original universal region 20, and optionally a sequence that is the same as the second loop-forming region 10'. This amplification primer 60 can hybridize to the complement of the double-extended loopable primer allowing for efficient amplification of the double-extended loopable primer. In some embodiments, more than one amplification primer can be used. In some embodiments, only a single primer per loopable primer nucleic acid sequence is used in the amplification step depicted in FIG. 3. In some embodiments, the use of a single primer sequence that will not hybridize to the initial loopable primer can help reduce nonspecific primer dimerization that could otherwise occur due to the presence of an amplification primer and remaining loopable primers. Thus, by selecting an amplification primer that has the same sequence as a portion of the loopable primer, one can further reduce the risk of primer dimerization or other nondesired hybridization events. Of course, the presence of the noncomplementary region 30 in the loopable primer 6 can be exploited in selecting such an amplification primer 60. In some embodiments, the amplification of the double extended loopable primer results in the selective amplification of double extended loopable primers having long insert sections over those with shorter or no foreign insert sections.

As will be appreciated by one of skill in the art, the amplification step can occur in situations in which additional background DNA or nucleic acid sequences are present. As will be appreciated by one of skill in the art, in embodiments in which the insert amplification primer only hybridizes to the universal region, there could be significant priming events to non target sections. However, the presence of the noncomplementary region in the loopable primer (and more specifically sequences complementary to these regions in the double-extended loopable primer) and in the amplification primer reduce the likelihood that this will occur.

Following the optional amplification step, at least a sub-population of the double-extended loopable primer can self-hybridize (as shown in FIG. 5). As noted above, self-hybridization of the double extended loopable primer does not have to occur for all species in a sample. Rather, self-hybridization need only occur for the shorter sequences (FIG. 5) which are to be reduced or "amplified over." Thus, in some embodiments, self-hybridization occurs for the structures in FIG. 5, but not for the structures depicted in FIG. 4. However, in some embodiments, the longer double-extended loopable primers also self-hybridize, as shown in FIG. 4.

As will be appreciated by one of skill in the art, the portions of the double extended loopable primer corresponding to the universal region 20 and the universal region complement 20' are capable of hybridizing to one another. The insert section 9 itself can then have the target nucleic acid sequence, or fragment thereof, which can be amplified by any of various reactions such as PCR. In some embodiments, insert amplification primer(s) 80 and/or 81 are used to amplify at least a portion of the insert. As will be appreciated by one of skill in the art, the size of the insert should be sufficient to allow amplification.

In embodiments in which self-hybridization of the longer double extended loopable primers is not required to occur (e.g., does not occur frequently or is not driving a subsequent selective amplification of longer insert sections over shorter insert sections), then the selective amplification is believed to occur due to the fact that the shorter double-extended loopable primers self-hybridize more rapidly than the longer double-extended loopable primers and thus are removed from subsequent rounds of amplification more quickly than the longer double-extended loopable primers. In such embodiments, while self-hybridization still occurs for the shorter double-extended loopable primers (e.g., primer dimers) it does not need to occur for the longer double-extended loopable primers. As the universal region and the universal region complement on these longer double-extended loopable primers (as depicted in FIG. 4) are separated by more nucleotides than the shorter double-extended loopable primer (FIG. 5), the self-hybridization of the longer double-extended loopable primers will take longer, allowing more time for the insert amplification primer to hybridize and extend. Thus, the self-hybridized structure for the longer double-extended loopable primer need not be formed to selectively amplify the longer double-extended loopable primer over the shorter double-extended loopable primer.

As will be appreciated by one of skill in the art, in embodiments in which whole genome amplification is being performed, the precise sequence within the insert section can be unknown. In light of this, it can be advantageous to use multiple insert amplification primers to make certain that one will prime and extend as desired. In some embodiments, a pool of insert amplification primers is used. In other embodiments, one insert amplification primer (and/or one set or more) is mixed with the solution containing the double-extended loopable primer. As will be appreciated by one of skill in the art, numerous such mixtures (e.g. 2-10, 10-100, 100-1,000, 1,000-10,000 or more) can be done in series or in parallel. Furthermore, the solution containing the double-extended loopable primer can be divided into parts so that the various reactions can be run in parallel.

As will be appreciated by one of skill in the art, not every loopable primer will necessarily hybridize to the target sequence as desired and in some embodiments a loopable primer duplex or primer dimer will be formed. Additionally, in some embodiments, loopable primers can hybridize to one another, also forming short amplification products. Additionally, in some embodiments, nonspecific hybridization or overly frequent hybridization of the 3' target specific region or of other sections (such as the universal region) of the various primers can hybridize to sections of the target nucleic acid sequence can occur such that only these smaller sections of the target nucleic acid sequence. One depiction of the above is shown in FIG. 5. In such a situation, rather than having target nucleic acid sequence (or a significant amount of it) between the universal region 20 and the complement to the universal region 20', there is an insignificant amount of target sequence between the two 20 and 20'. As shown in FIG. 5, when the universal region 20 and universal region complement 20' hybridize together under this situation, the insert section 109 in the complex 108 is relatively small. In some embodiments, there is a nucleic acid sequence 51 in the insert section between the 3' target specific region 50 and its complement 52. This nucleic acid sequence 51 need not be present and, if it is present, is relatively short. In some embodiments (when a sufficiently large insert is present), the insert section 109 (including sequence 51) is not more than 10 kb in length. In some embodiments, the insert section 109, while still capable of allowing amplification does so with relatively less efficiency than the double-extended loopable primer complex 8 shown in FIG. 4. As such, relative amplification of the product 8 shown in FIG. 4 can be achieved compared to amplification of the resulting product 108 shown in FIG. 5. As will be appreciated by one of skill in the art, this distinction between the two resulting products can reduce the role or impact that nonspecific primer interactions can have, e.g. primer dimers on the ability to identify amplified sequence target. That is, this distinction can generally improve target detection by reducing the impact of nucleic acid structures (or products) in which a significant or substantial amount of target DNA has not incorporated between the two primers. As will be appreciated by one of skill in the art, when the 3' target specific region 50 and 52 are complementary to one another (e.g. when only a single palindromic sequence is used) they can hybridized together and the sequence 51 need not be present (e.g., when the double-extended loopable primer is just a primer dimer). In embodiments in which the 3' target specific region is a degenerate region or sequence, then sections 50 and 52 need not, and often will not, be complementary to one another.

While not depicted in FIGS. 4 and 5, one of skill in the art will readily recognize that in the embodiments in which a self-hybridized structure is not created for the longer double-extended loopable primer, that the insert amplification primers 81 and 80 can bind to the "open" double-extended loopable primer, and can bind to the universal region or other section of the loopable primer. In some embodiments, one of the insert amplification primers comprises, consists, or consists essentially of a universal region, while the second insert amplification primer primes in the insert. In some embodiments, both insert amplification primers hybridize within the insert section. In some embodiments, neither of the insert amplification primers prime or overlap with any section of the loopable primer.

Double-Extended Loopable Primers with Additional Specific Sequences

Figure 6:
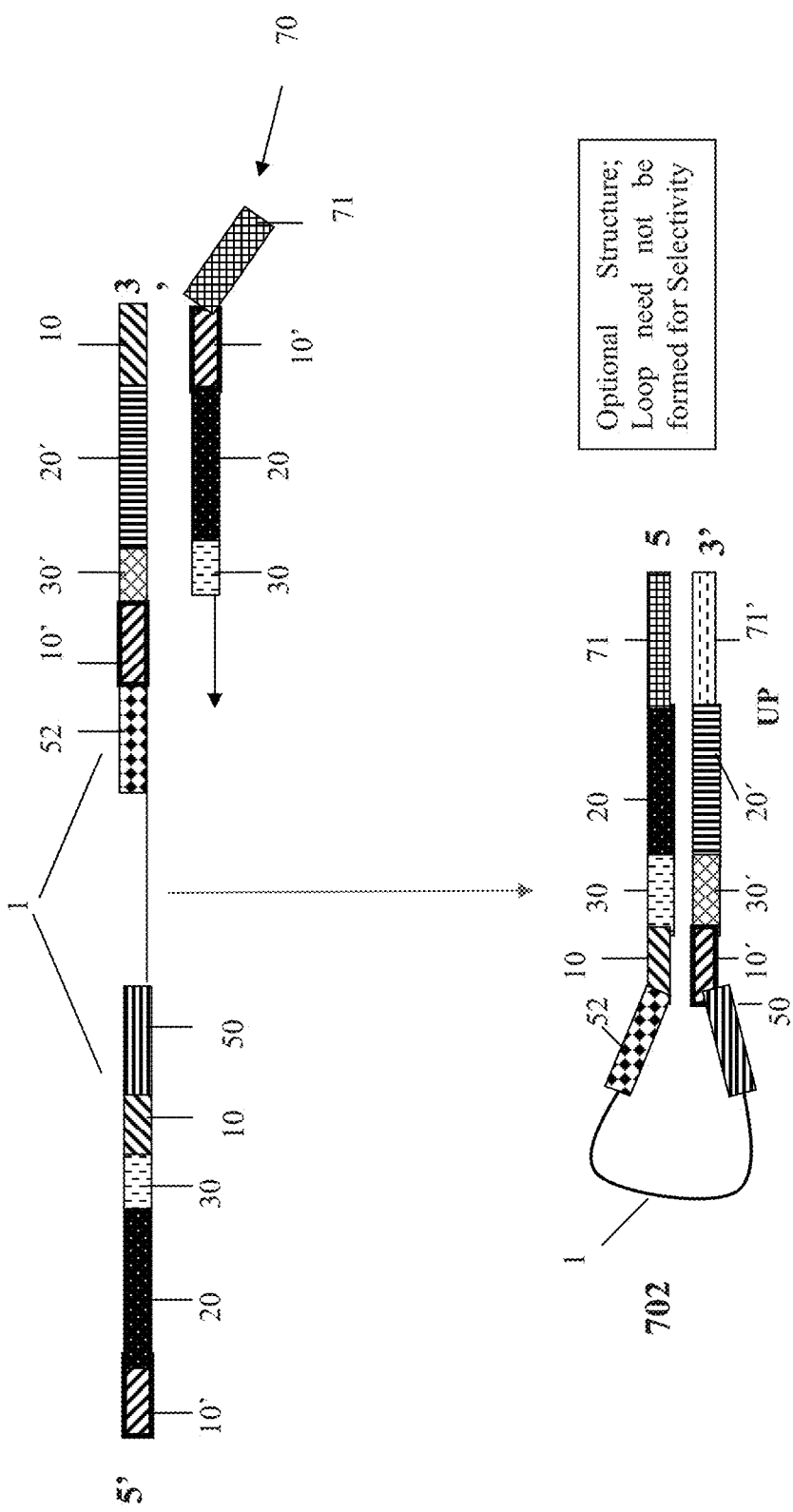
FIG. 6 is a depiction of some embodiments in which various double-extended loopable primers are self-hybridized.

As will be appreciated by one of skill in the art, in some embodiments, it is desirable to have specific sequences on the 5' and/or 3' end of the nucleic acid sequence that have been amplified, such as the double-extended loopable primer. Examples of such specific sequences include zip-code sequences, as described in U.S. Pat. Pub. No: 2006/0014191 (the entirety of which is hereby incorporated by reference). One option for achieving this is shown in FIG. 6 and FIG. 7 (which depict the self-hybridized embodiments only, although one of skill in the art can adjust the figures for the non-self-hybridized embodiments as well). In such embodiments, rather than (or following) the amplification step depicted in FIG. 3, involving the amplification primer 60, one performs an amplification step to add a desired sequence (e.g. 71) to one end of the double-extended loopable primer via a different primer 70. This process, and the resulting product 702, are shown in FIG. 6 for a double-extended loopable primer that has a significant amount of target nucleic acid sequence in it, and in FIG. 7, for a double-extended loopable primer that has an insignificant amount of target DNA in it.

In some embodiments, there is a first amplification primer 70 which, while including the universal region 20 (and optionally the noncomplementary region 30), includes an additional section 71. This section 71 allows one to customize the end(s) of the double-extended loopable primer. As will be appreciated by one of skill in the art, section 71 is not a "noncomplementary" region, as defined herein, rather, it is a sequence that is not complementary to the sequence that the amplification primer 70 is hybridized to. The ability to have different sequences on each end of the nucleic acid segment (which can be achieved by using two different primers with different sections 71) can be useful in some sequencing applications. Thus, the above amplification primer 70 can be used in these situations. The primer 70 can include the noncomplementary region 30 and the universal region 20. As will be appreciated by one of skill in the art, different primers 70, each having a different section 71, can be added to specific double extended loopable primers, allowing various double extended loopable primers to be combined and processed in parallel, while still being able to identify the specific double extended loopable primer. In some embodiments, two different primers or different sections can be added to each end.

As shown in the lower section of FIG. 6, when the target nucleic acid sequence 1 is included, amplification proceeds from these two primers to produce a double extended loopable primer (702). Of course, an actual looped structure need not be formed and desirable reaction kinetics can be sufficient to achieve the desired reactions.

In contrast, as shown in FIG. 7, in those situations in which very little or no target nucleic acid sequence is included between the universal region 20 and its complement 20' (or the first loop forming region 10 and the second loop forming region 10'), the resulting structure has a relatively smaller insert section resulting in relatively less amplification through the use of insert amplification primers (802) (as noted above, this can be due to the faster hybridization kinetics due to the shorter linker and/or due to, for example, the smaller size of the insert structure which can physically limit processing of this area.)

Additional Alternative Aspects

In some situations, after incorporation of a universal region, universal primers can still have a problem of having some homology with internal sequences in highly complex populations of long gDNA fragments from the whole genome. Where the concentration of the universal primers are typically on a μM scale, even partial matches of the 3' end of the universal primers with internal sequences of gDNA fragments can generate shorter products. These shorter products can be preferentially amplified by high concentrations of universal primers. Thus, some of the present embodiments can be used to limit the generation of these short products from primer-dimers or spurious internal priming. In some embodiments long tracts of dT bases can be used in the loopable primer (as a noncomplementary region for example) for the above reason and because the frequency of poly dT in the middle of gDNAs can be low. In other embodiments, tracts of sequences rarely found in the target genome are used as a noncomplementary region.

As will be appreciate by one of skill in the art, while the 3' target specific region often includes a random or degenerate region, in some embodiments, the sequence is a specific sequence or collection of specific sequences. In some embodiments, the looped section of the loopable primer (including the stem) can include additional sequence sections to those described above. In other embodiments, the looped section only includes those depicted in FIG. 1A. Additionally, as will be appreciated by one of skill in the art, some of the presently disclosed techniques can be applied to RNA amplification as well, for example, by including an initial reverse transcription step.

As will be appreciated by one of skill in the art, in some embodiments, a noncomplementary region is used throughout numerous primers, allowing for multiple primers, such as primers including universal, random, or degenerate regions, to be used with a reduced risk of undesired priming events. This can be useful in multiplexed reactions in which numerous different starting primers are employed.

In some embodiments, the above methods can allow for a significant amount of amplification to occur. In some embodiments, the amplification is of nucleic acid sequences of a significant length (e.g., 200 or more nucleic acids). In some embodiments, the amplification of these lengths of target nucleic acid sequences, across a genome's worth of nucleic acid sequence, is achieved. In some embodiments, at least a fraction of the genome is amplified, e.g. 0-1, 1-5, 5-10, 10-20, 20-30, 30-40, 40-50, 50-60, 60-70, 70-80, 80-90, 90-95, 95-99, or 99-100% of the genome is amplified. In some embodiments, at least some fraction of the fraction amplified is of the desired length, e.g. 0-1, 1-5, 5-10, 10-20, 20-30, 30-40, 40-50, 50-60, 60-70, 70-80, 80-90, 90-95, 95-99, or 99-100% is at least 200 bp in length.

In some embodiments, the amount of amplification across a genome is substantially similar. In some embodiments, the amount of amplification for the various target nucleic acids sequences is the same. In other words, sequences A-Z are all amplified to a similar extent so that the resulting ratio of product nucleic acid sequences is the substantially the same for sequences A-Z. In some embodiments, the ratios are maintained in a qualitative manner (e.g., there is more of sequence A than sequence B).

In some embodiments, the amount of amplification of the desired fragments that is achieved is substantial. For example, amplification of the initial product over 30 fold can be achieved, e.g. 30-100, 100-1000, 1,000-3000, 3000-10,000, 10,000-50,000, 50,000-100,000, 100,000-500,000, 500,000-800,000, 800,000-1,000,000, 1,000,000-10,000,000 fold or more. In some embodiments this is achieved with a reduced amount of primer dimer formation and/or spurious priming. In some embodiments, the amount of primer dimers is reduced by at least some amount, e.g. 0-1, 1-5, 5-10, 10-20, 20-30, 30-40, 40-50, 50-60, 60-70, 70-80, 80-90, 90-95, 95-99, or 99-100%.

As noted above, some of the embodiments can be advantageously used when random and/or degenerate priming regions are employed at the 3' target specific region of the primer, when universal primers are used, or when both aspects are used. Moreover, in some embodiments, further benefits can be obtained when numerous such primers (or other non-loopable primers) are combined within a reaction (such as in multiplexed or subsequent amplification or extension reactions). As such, as noted above, some of the embodiments can be useful for whole genome amplification. However, not all of the disclosed embodiments are limited to such applications. Even amplification reactions that do not include random regions, or do not involve whole genome amplification can benefit from some of the above embodiments. For example, some of the above embodiments will reduce the number or amount of relatively short nucleic acid sequences that are amplified from a target. As will be appreciated by one of skill in the art, these shorter sequences can be problematic for a variety of reasons (e.g. since they are shorter, they will dominate subsequent amplification reactions). Additionally, the insertion of the noncomplementary region generally allows for one to use either a random, specific, or mix thereof, region for target hybridization, while reducing the likelihood that the target sequence will hybridize too frequently or nonspecifically.

In some embodiments, the loopable primers and relevant methods are employed in massively multiplexed procedures in which various loopable primers are employed. As will be appreciated by one of skill in the art, the above embodiments employing degenerate ends at the 3' target specific region of the probe is one form of multiplexing. However, in some embodiments, different sequences are also employed within the loopable section and/or the stem section so as to provide a degree of separation or distinctness among the amplified products. In some embodiments, these different sequences are in the universal priming section, a tag sequence, or other additional section added to the loopable primer. In some embodiments, the number of primers having these different sequences (apart from differences in the 3' target specific region) are at least 2, if not more, for example, 2-5, 5-10, 10-20, 20-30, 30-50, 50-100, 100-200, or more primers can be used. In some embodiments, the primers can include specific bar-code sequences to allow for ease of identification. In some embodiments, these sequences are the same as the stem forming sequences (e.g. the first and second loop forming regions).

In some embodiments, the loopable primer and various embodiments disclosed herein are used for assisting in forensic analysis. In some embodiments, the loopable primer and various embodiments disclosed herein are employed in amplifying a target nucleic acid sequence for DNA fingerprinting. In some embodiments, the loopable primer and various embodiments disclosed herein are employed in amplifying short tandem repeats ("STR") from a sample that is to be identified or matched to another sample. In some embodiments, the loopable primer includes a sequence that can be used to amplify a STR locus. In some embodiments, the insert amplification primer includes a sequence that can be used to amplify a STR locus.

In some embodiments, the double-extended loopable primer is created as described by any of the embodiments described herein. Once the double extended loopable primer is created, and optionally amplified by an amplification primer, one or more insert amplification primers can be used to amplify the insert section. In some embodiments, the insert amplification primers will hybridize to sections upstream or downstream of one or more STR loci to be amplified. In some embodiments, the insert amplification primer comprises or consists of a STR primer. Thus, in some embodiments, the double-extended loopable primer can be used for efficient amplification of a target or target genome and the use of STR-primers (or insert amplification primers that can be used to amplify a STR locus) can be used to further selectively amplify and/or detect the presence of specific STRs in a sample. In some embodiments, the insert amplification primer is a STR-primer that can amplify the locus of one or more of the 13 standard STRs examined for DNA fingerprinting. In some embodiments, the insert amplification primer is a STR-primer that can amplify the locus of one or more of the currently 13 standard STRs examined for DNA fingerprinting.

In some embodiments, rather than using a STR specific aspect towards the end of the process, the loopable primer itself comprises an aspect that will direct it to the amplification of STRs or sequences around STRs. For example, in some embodiments, the 3' target specific region, rather than being a random or degenerate region, comprises or consists of a STR-primer sequence that can be used to amplify a STR locus. Apart from this modification, the remaining steps can include any of those disclosed herein. In such an embodiment, the insert amplification primers do not need to be STR primers (although they can be).

A "STR-3' target specific region" denotes a 3' target specific region that will serve as a STR-primer (and thus can be used to amplify a STR locus).

A "STR-primer" is a primer that can be used to amplify a STR locus.

In some embodiments, the locus is one or more of TH01, TPOX, CSF1PO, vWA, FGA, D3S1358, D5S818, D7S820, D13S317, D16S539, D8S1179, D18S51, D21S11, D2S1338, D3S1539, D4S2368, D9S930, D10S1239, D14S118, D14S548, D14S562, D16S490, D16S753, D17S1298, D17S1299, D19S253, D19S433, D20S481, D22S683, HUMCSF1PO, HUMTPOX, HUMTH01, HUMF13AO1, HUMBFXIII, HUMLIPOL, HUMvWFA31, Amelogenin, D12s391, D6S1043, SE33, or any combination thereof. In some embodiments, the locus is one or more of CSF1PO, FGA, THO1, TPOX, vWA, D3S1358, D5S818, D7S820, D8S1179, D13S317, D16S539, D18S51, D21S11, D19S433, and D2S1338. In some embodiments, the locus is a "CODIS loci" or "CODIS locus." This refers to the STR loci designated by the FBI's "Combined DNA Index System." Thirteen core STR loci are TH01, TPOX, CSF1PO, vWA, FGA, D3S1358, D5S818, D7S820, D13S317, D16S539, D8S1179, D18S51, and D21S11. (See, e.g., Butler, Forensic DNA Typing, Academic Press (2001), at page 63.)

In some embodiments, more than one locus is amplified in one reaction. In some embodiments, two, three, four, five, six, seven, eight, nine, ten, eleven, twelve, thirteen, fourteen, fifteen, sixteen, seventeen, eighteen, nineteen, twenty or more loci are co-amplified. In some embodiments employing multiplex co-amplification, not all of the primer pairs comprise a high stability primer.

After amplification, the products from the PCR reactions can be analyzed, resolved, and/or characterized by any of a variety of methods known in the art. For example, PCR reactions can be analyzed by denaturing samples and separating using gel electrophoresis or a capillary electrophoresis protocol. The results from this can then allow one to determine the number of repeats of the STR sequence that are present.

Aspects of the present teachings may be further understood in light of the following examples, which should not be construed as limiting the scope of the present teachings in any way.

EXAMPLE 1

Amplification of gDNA

This example describes how one can employ loopable primers for the amplification of a substantial portion of a genome.

First, one obtains, provides, or is provided a sample that includes genomic DNA. One can then generally isolate the genomic DNA in the sample from various non-DNA impurities in the sample. Following this, one can add a loopable primer to the solution containing the gDNA. The loopable primer can include a degenerate section and therefore actually comprise numerous individual primers, each having a different 3' target specific sequence. The conditions of the reaction will be set so that the loopable primer can hybridize to the gDNA, while the loopable primer is in its looped conformation. The loopable primer is then extended to eventually form a double-extended loopable primer.

Following this, an amplification step can be performed with an amplification primer. The amplification primer includes a section that is substantially identical in sequence to the universal region and, optionally the noncomplementary region (if present) in the original loopable primer. Optionally, an amplification primer can also include a sequence that is substantially identical to the second loop forming region. PCR can then be performed on the solution, using this amplification primer.

Following this, a digest is performed on the solution so that any single stranded primers are eliminated. This can be achieved via exonuclease I.

Following this, the conditions of the solution are adjusted, if necessary, to allow the shorter double-extended loopable primers to self-hybridize.

Insert amplification primers are then added to the solution. The insert amplification primers can be degenerate primers or universal primers.

The amplified double-extended loopable primer can also be divided into separate containers (such as wells) and a specific insert amplification primer (or primer set) added to each container to allow amplification to occur based on that specific insert amplification primer (or set). Numerous such insert amplification primers can be used in series or parallel in the separate containers. A PCR is performed on the solution (or more specifically for each solution) under conditions that allow the annealing and extension of the insert amplification primers, while keeping the conditions such that the double-extended loopable primer is self-hybridized.

The above steps will result in the amplification of the target nucleic acid sequence.

EXAMPLE 2

Modification for Distinguishable Ends of the Product

This example provides an additional option for manipulating the amplified DNA for subsequent ease of use in various sequencing techniques. Using Example 1 as the general template, one can add an additional step, after the creation of the double-extend loopable primer, to add a specific sequence on the tail of the nucleic acid sequence being amplified. In some embodiments, this tail sequence allows one end of the nucleic acid sequence to have a specifically desired nucleic acid sequence, which can be advantageous in various sequencing methods.

This specific tail sequence can be added through the use of a second amplification primer that has a tail section that will not effectively hybridize to the double-extended loopable primer (or the complement thereof). Alternatively, the tail section can be added in a subsequent reaction, after an amplification of the double-extended loopable primer.

The addition of the specific tail sequence can be achieved before the formation of the self-hybridized structure, or during or after the amplification of the target nucleic acid sequence in the insert section (which is achieved in Example 1 via the insert amplification primers).

EXAMPLE 3

Formation of Double-Extended Loopable Primers, Two Different Loopable Primers

This example demonstrates one embodiment in which RNA can be amplified by two loopable primers.

Loopable primers are added in excess to a solution that includes a target sequence to be amplified. The loop section of the loopable primer include sequences of poly(T) (as the noncomplementary region) and a universal region site in the loop. The sequences of the primers are shown in Table 1. The last four primers in Table 1 include two sets of loopable primers, one having 6 and the other having 8 nucleic acids in the 3' target specific region.

TABLE 1

| Primer Sequences | |
|---|---|
| UF-T10 | GTCGACTGCGTGGAGTCGGCTTTTTTTTTT (SEQ ID NO: 1) |
| UR-T10 | TCATGATCCGTGGAGTCGGCTTTTTTTTTT (SEQ ID NO: 2) |
| (N) 8-T10-UP-RP | TCATGATCCGTGGAGTCGGCTTTTTTTTTT GATCATGANNNNNNNN (SEQ ID NO: 3) |
| (N) 6-T10-UP-RP | TCATGATCCGTGGAGTCGGCTTTTTTTTTT GATCATGANNNNNN (SEQ ID NO: 4) |
| (N) 8-T10-UP-FP | GTCGACTGCGTGGAGTCGGCTTTTTTTTTT CAGTCGACNNNNNNNN (SEQ ID NO: 5) |

TABLE 1-continued

Primer Sequences (N) 6-T10-UP-FP  GTCGACTGCGTGGAGTCGGCTTTTTTTTTT
                CAGTCGACNNNNNN
                (SEQ ID NO: 6)

Next, the double extended loopable primer are synthesized by the other looped primer. As will be appreciated by one of skill in the art, this can occur concurrently with the above process.

The length of the poly(T) (noncomplementary region) and universal region are long enough to form stable stem structure upon self-hybridization (as shown in FIG. 5), so that self-hybridized double-extended loopable primers that only include short fragments of target DNA are not be further PCR amplified.

The amplification primers are then added to the solution and the double-extended loopable primers are then amplified by PCR. The cDNAs are amplified by 20 cycles of PCR by two amplification primers that include universal regions (FP-T10) and the noncomplementary region (see Table 2 for specific protocols and conditions).

The result of the above steps is the amplification of the double-extended loopable primer, the shorter products of which can then be allowed to self-hybridize. The self-hybridized double-extended loopable primers that include longer target nucleic acid sections (in which about 1 kb or more has been incorporated) have a larger insert section that will allow subsequent insert amplification primers to anneal within the loop structure.

In an alternative example, following the amplification of the double-extended loopable primer, while the shorter double-extended loopable primers can self-hybridize, the longer double extended loopable primers do not self-hybridize. Self-hybridized structures are not amplified further; thus, selective amplification between short and long double-extended loopable primers can be achieved simply by the selective amplification of those double-extended loopable primers that are not self-hybridized.

In yet another alternative example, the selective amplification of the longer double-extended loopable primer over the shorter double-extended loopable primer occurs during the amplification of the double-extended loopable primer. As the shorter double-extended loopable primers can self-hybridize, the longer double extended loopable primers do not self-hybridize. Self-hybridized structures are not amplified further; thus, selective amplification between short and long double-extended loopable primers can be achieved simply by the selective amplification of those double-extended loopable primers that are not self-hybridized.

TABLE 2

| protocol | Volume | Stock Concentration | Final Concentration | | 10x mixture |
|---|---|---|---|---|---|
| Step 1 RT | | | | | 10 |
| 10x cDNA Archiving Kit buffer | 0.5 | 10 | 1 | | 5 |
| MMLV 50 u/ul | 1 | 50 | 10 | (10 u/ul) | 10 |
| 100 mM dNTP | 0.25 | 100 | 5 | (100 mM/uL) | 2.5 |
| (N)8-T10-UP-RP (20 uM) | 0.25 | 20000 | 1000 | (1 uM) | 2.5 |
| total RNA 10 ng/ul samples | 2 | 10 | 4 | | 20 |
| H2O | 0.25 | 0 | 0 | | 2.5 |
| MgCl2 (25 mM) | 0.75 | 25 | 3.75 | (3.4 mM) | 7.5 |
| total volume | 5 | | | | |
| (50 C, 1 sec- 42 C, 20 sec-20 C, 30 sec) 30 cycles, 85 C, 5 min | | | | | |
| step 2 extension and pre-PCR | | | | | 10 |
| 2x UMM (No UNG) | 2.5 | 2 | 1 | | 25 |
| RT-template | 1 | 0 | 0 | | |
| (N)8-T10-UP-FP (20 uM) | 0.5 | 20 | 2 | (2 uM) | 5 |
| UF-T20 100 uM | 0.1 | 100 | 2 | (2 uM) | 1 |
| UR-T20 100 uM | 0.1 | 100 | 2 | (2 uM) | 1 |
| AmpliTaqGold 5 u/ul | 0.25 | 5 | 0.25 | (0.25 u/ul) | 2.5 |
| dNTP 100 mM | 0.1 | 100 | 2 | (2 mM) | 1 |
| MgCl2 25 mM | 0.2 | 25 | | | 2.5 |
| total volume | 5 | | | | 40 |
| 95 C 10 min | | | | | |
| (95 C 1 sec-42 C 1 min) 10 cycles | | | | | |
| (95 C 1 sec-65 C 1 min) 10 cycles | | | | | |

While the above protocol can be used to amplify target nucleic acid sequences, the use of separate forward and reverse loopable primers can complicate the results. In light of this, a single degenerate loopable primer was examined and the experiment and results are outlined in Example 4.

EXAMPLE 4

Formation of Double-Extended Loopable Primers

Figure 8:
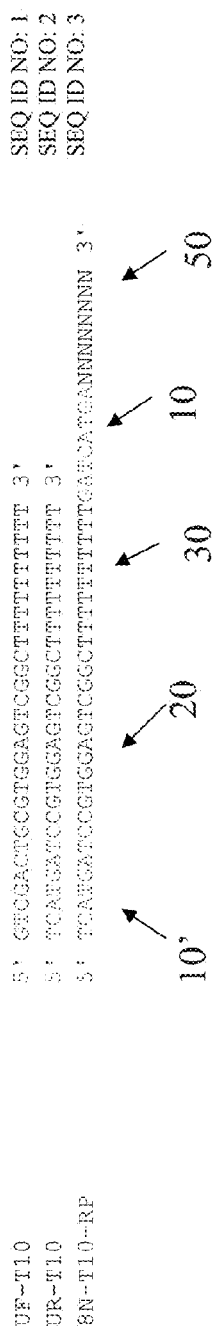
FIG. 8 is a depiction of various primers, denoting the various subparts of the primers, such as the first and second loop forming regions, the noncomplementary region, a universal region and a degenerate or 3' target specific region.

This example demonstrates how a loopable primer (which included a degenerate 3' target specific portion) was used for the amplification of various target sequences (in the form of double extended loopable primers). The various primers used (including the loopable primer) are shown in FIG. 8. The "8N-T10-RP" primer was the loopable primer sequence that was employed. The repeat of "N" at the 3' end denotes a degenerate end, representing all possible sequence combinations of A, T, G, and C for 8 nucleotides of sequence. Thus, this primer sequence represents $4^8$ different primer sequences in this section of the loopable primer. The target sample was CEPH gDNA (human, parts #4312660, Applied Biosystems).

The particular details of the protocol are outlined in Table 3. First, the loopable primer was added to the solution containing the target sequence. The loopable primer hybridized to the target. The loopable primer was then extended multiple times so that the amplified products included both a universal region sequence and a universal region complement (and therefore were double-extended loopable primers). The specific parameters performed for achieving this are outlined in Table 3, step 1. Following this, the solution was treated with Exo I to digest random primers (outlined in Table 3, step 2). Following this, pre-PCR was carried out on the solution using a single primer, UR-T10 (outlined in Table 3, step 3).

TABLE 3

| Whole genome Amplification | volume (uL) | stock concentrations |uM) | Final concentration (uM) | Final cocentration |
|---|---|---|---|---|
| step 1 extension and pre-PCR | | | | |
| 10xPCR buffer II | 1 | 10 | 1 | |
| DNA-template (95 C 5 min pre-denature) | 2 | 0 | 0 | |
| N8-UR-T10 (100 uM) | 2 | 100 | 20 | (20 uM) |
| AmpliTaq 5 u/ul | 1 | 5 | 0.5 | (0.5 Unit/ul) |
| dNTP 100 mM | 0.5 | 100 | 5 | (5 mM) |
| MgCl2 25 mM | 1.2 | 25 | 3 | (3.0 mM) |
| H2O | 2.3 | | | |
| total volume | 10 | | | |
| 95 C 1 min | | | | |
| (95 C 15 sec –35 C 4 min –65 C 4 min) 10 cycles | | | | |
| step 2 PCR clean up with Exo I digestion of random primers | | | | |
| 10 ul above product + 2 ul ExoSAP | | | | |
| 37 C 15 min, 85 C 5 min | | | | |
| step 3 further extension and pre-PCR | | | | |
| 10xPCR buffer II | 2 | 10 | 1 | |
| step 2 products | 12 | | 0 | |
| UR-T10 100 uM | 2 | 100 | 10 | (10 uM) |
| dNTP 100 mM | 0.5 | 100 | 2.5 | (2.5 mM) |
| MgCl2 100 mM | 1 | 25 | 1.25 | (1.25 mM) |
| AmpliTaq 5 u/ul | 1 | 5 | 0.25 | (0.25 u/ul) |
| H2O | 2.2 | | 0 | |
| total volume | 20 | | | |
| 95 C 1 min | | | | |
| (95 C 15 sec –65 C 4 min) 30x | | | | | step3 product 20 ul + dH2O 80 ul = 100 ul (1:5dilution)

Figure 10:
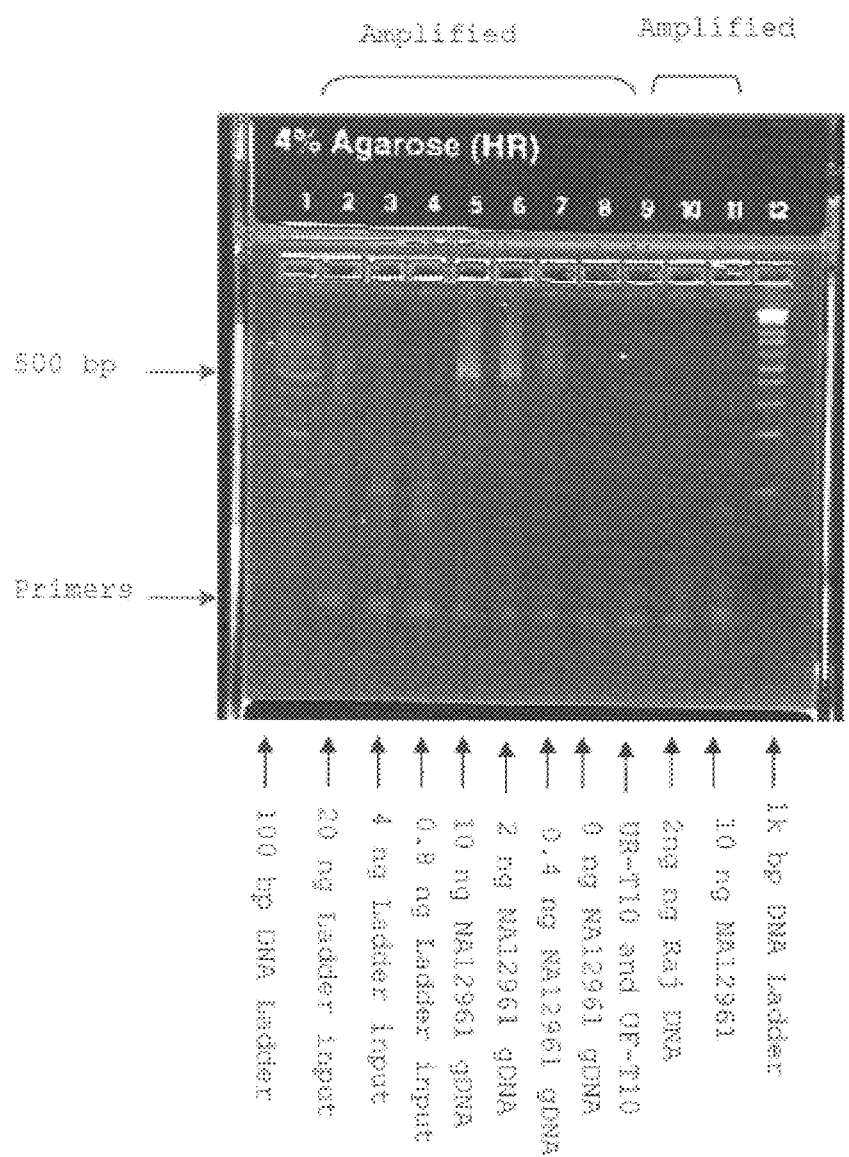
FIG. 10 is a depiction of a gel showing the double-extended loopable primer products produced by some of the present embodiments

The above protocol resulted in the selective amplification of a large amount of target nucleic acid sequences in the double-extended loopable primers. The results are displayed in FIG. 10, which is a gel on which the product from this Example was run. The results shown in the gel demonstrate that varying starting amounts of the genomic DNA (0.4-10 ng), while resulting in various amounts of product, all displayed significant amplification (as shown by the strong bands at 2 and 10 ng). As will be appreciated by one of skill in the art, the target DNA was amplified as part of the double extended loopable primer. The fact that significant portions of the target DNA were amplified is demonstrated by the relatively large size of the amplified product (larger than the primers and significant amounts above 500 bp). This confirms that this aspect of the technique functions as described herein. Additionally, FIG. 10 demonstrates the selective and effective amplification of larger fragments over smaller fragments. As can be observed in FIG. 10, significant amounts of amplification was demonstrated at the larger ranges (the upper part of the gel, over and around 500 bp), further demonstrating the effectiveness of this technique in selectively amplifying relatively large sections.

The increase in amplification ability of the above example is quantitated in some of the examples below; however, it is noted that the general technique can amplify an input nucleic acid sequence by about 3000 fold (input of 10 ng and output of 30 micrograms) to several hundred thousand fold. In contrast to this, other amplification techniques available in the art result in only a 30 fold amplification.

EXAMPLE 5

Distinguishable Primer Ends

This example demonstrates one option for adding a different primer tail onto the double-extended loopable primer. To the products produced in Step 3 in Example 4, an additional amplification primer was added (SEQ1-U-T10) as well as a primer with a second tail end, but was otherwise similar to the amplification primer (e.g. SEQ2-U-T10). The solution was then PCR amplified as shown in Table 4.

TABLE 4

| Two primer PCR for Sequencing application | volume (uL) | stock concentrations (uM) | Final concentration (uM) | Final concentration |
|---|---|---|---|---|
| 10xPCR buffer II | 2 | 10 | 1 | |
| step 3 products (1:5 dilution) | 2 | | 0 | |
| SEQ1-U-T10 100 uM | 1 | 100 | 5 | (5 uM) |
| SEQ2-U-T10 100 uM | 1 | 100 | 5 | (5 uM) |
| dNTP 100 mM | 0.5 | 100 | 2.5 | (2.5 mM) |
| MgCl2 100 mM | 1 | 25 | 1.25 | (1.25 mM) |
| AmpliTaq 5 u/ul | 1 | 5 | 0.25 | (0.25 u/ul) |
| H2O | 2.5 | | 0 | |
| total volume | 11 | | | |
| 95 C 1 min | | | | |
| (95 C 15 sec –65 C 4 min) 15x | | | | |

This process added a different sequence (the 5' end of UR-T10) to one end of the amplified sequence in order to allow for various sequencing techniques to be employed on the amplified sequence.

EXAMPLE 6

Insert Section Amplification

This example presents the results of a study that examined the effectiveness of the techniques discussed in Example 4, when the additional step of the loop amplification was performed. Furthermore, this example also provides a demonstration of the additional step of the actual insert section amplification step, via a TAQMAN™ assay.

In order to test the effectiveness of the amplification of the target nucleic acid sequences and the ability of the insert amplification step to function as described above, the presence of a target sequence in the amplified target nucleic acid sequences (the double-extended loopable primer) was examined via a TAQMAN™ gene expression assay for Rnase P. The details of the Rnase P protocol are shown in Tables 5.

TABLE 5

| Rnase P assay | stock volume (uL) | concentrations |
|---|---|---|
| 2x UMM Mix (NO UNG) | 5 | 2x |
| step 3products (1:5 dilution) | 2 | |
| 20x RNase P Mix of primers and TaqMan probe | 0.5 | 20x |
| H2O | 2.5 | |
| total volume | 10 | |
| 95 C 1 min | | |
| (95 C 15 sec –60 C 1 min) 40x | | |

Table 6 summarizes the results between the experimental data and the mock experiment controls. A comparison of the amplified and mocked (keep in −20 C) reactions was made to determine effectiveness of general technique.

TABLE 6

| | 10 ng CEPH DNA inputs | | | | | |
|---|---|---|---|---|---|---|
| Amplification folds | Ct of Rnase P | Ct of Rnase P | NTC | NTC | Amplified DNA ug | Amplified DNA ug |
| UR-T10 | 19.31 | 19.24 | 35.82 | 35.81 | 29.03 | 30.47 |
| mock UR-T10 | 30.81 | 30.42 | 35.66 | 35.89 | 0.01 | 0.01 |
| Amplification folds | 2902 | 2323 | 1 | 1 | | |

As shown in Table 6, the results from the RNase P assay demonstrated that the amplification fold of the above steps (Example 4 and the present example) was between 2902-2323 for a single primer PCR in 30 cycles. The yield noted above was calculated as follows:

Amplification fold=$2^{(Ct\ of\ mock-Ct\ of\ UR-T10)}$= $2^{(30.81-19.31)}$=2902.

The yield of DNA at Step #3=amplification fold×gDNA input=2902*10 ng=29.02 µg. Alternatively, using the standard curve to determine yields results in the following:

Yield of DNA at Step #3=10 ng*50 (dilution factor)× $2^{(Ct\ of\ 10\ ng\ standard \times Ct\ of\ UR-T10)}$ =10× 50×$2^{(25.17-9.31)}$=29030 ng=29.03 µg.

The Ct of Rnase P for 5 ng was 26.15, for 10 ng was 25.17 and for 20 ng was 24.08. As only 2 µL of the 100 µL produced in step #3 was used for the RNase P quantification, there was a 50-fold dilution factor. Adjusting for this, given a 10 ng CEPH gDNA input at step 1, the technique resulted in 29-30 µg of amplified DNA fragments.

Figure 9:
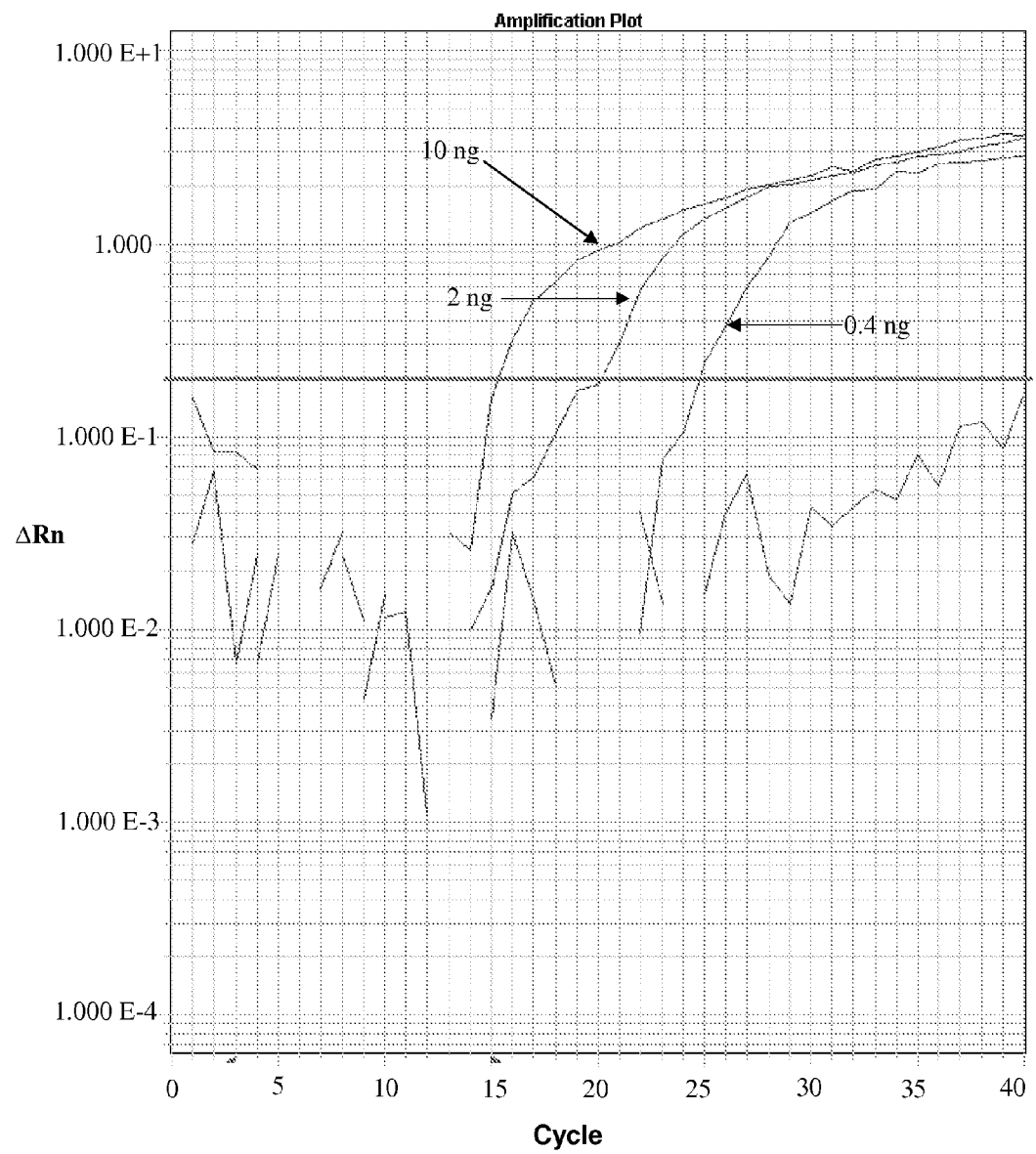
FIG. 9 is an amplification plot showing the relationship between initial starting material and the number of cycles required to pass a threshold.

In addition to the quantitative results demonstrated above, FIG. 9 further demonstrates the ability of some of the various embodiments to achieve various desired amounts of amplification. FIG. 9 demonstrates that the technique displayed a desired decrease in cycle threshold as increasing amounts of starting target DNA are used (from 0 to 10 ng of NA12961 gDNA (Coriell DNA purchased from Coriell Institute). As such, it is clear that the technique appears to function as noted herein.

EXAMPLE 7

Effectiveness of Exo I Digest, and the Effectiveness of Variously Sized 3' Target-Specific Portion Regions in the Loopable Primer The present example demonstrates the results of modifying various variables in Example 4. Specifically, the experiment in Example 4 was repeated with and without the Exo I digest and using variously sized 3' target specific regions (8-12 nucleic acids of degenerate sequence). The results for these varied conditions are presented in FIG. 11 (with no Exo I digest) and FIG. 12 (with an Exo I digest).

Figure 11:
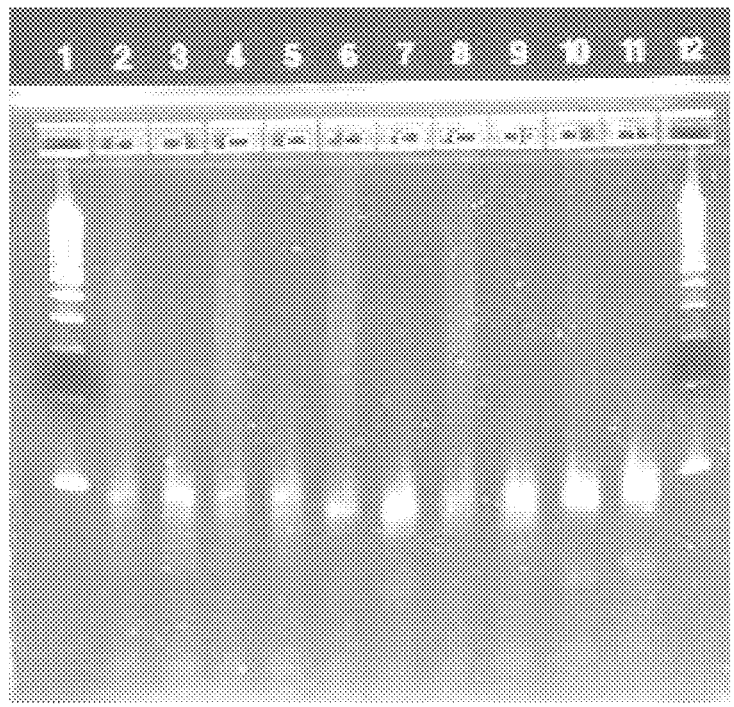
FIG. 11 is a depiction of gel demonstrating that amplification of the target nucleic acid sequence within the double-extended loopable primer was achieved, across a variety of variables (including without an Exo I cleaning step).

The smears in the lanes in the gel in FIG. 11 demonstrate that, for a method similar to that described in Example 4 (except that no Exo I digest step was performed), selective amplification of relatively large sized fragments of the target nucleic acid sequence occurred for 8, 9, 10, 11, and 12 mer sized 3' target-specific portion (e.g., degenerate) regions on the looped primer. This is displayed by the high amount of product distributed in the upper section of the experimental lanes (indicated by "20") compared to the negative control lanes (indicated by "0"). It is clear from the results in FIG. 11 that a variety of lengths of 3' target-specific portions or degenerate regions will work on the loopable primer.

Figure 12:
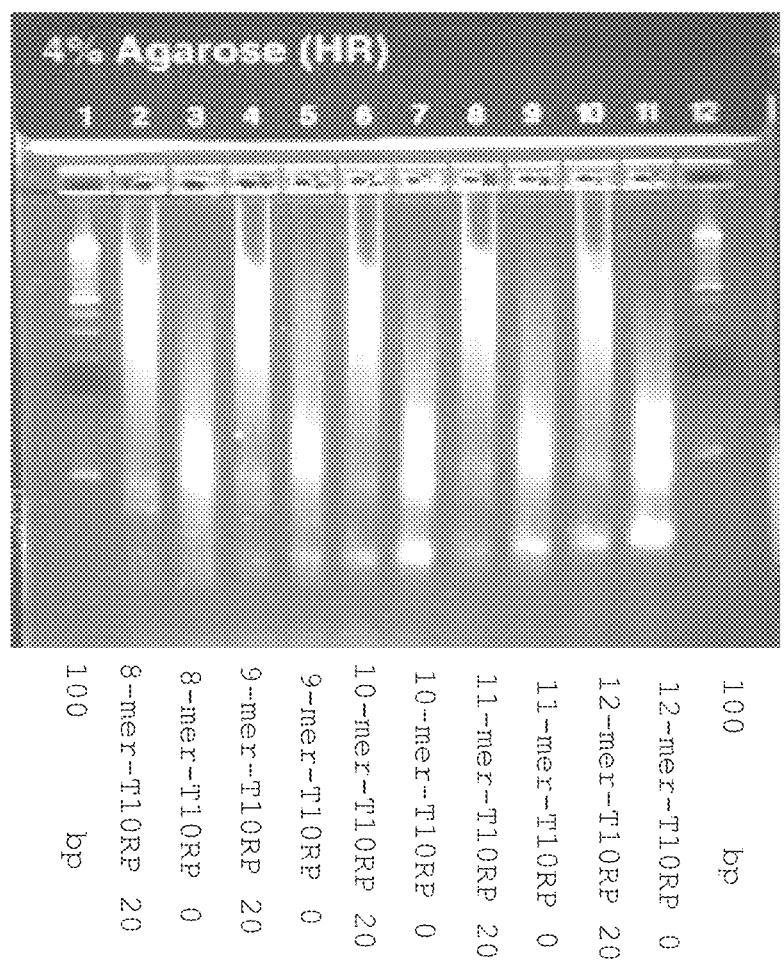
FIG. 12 is a depiction of a gel demonstrating that amplification was achieved under a variety of conditions (including with an Exo I cleaning step).

The results shown in the gel in FIG. 12, which included the Exo I digestion step (step 2) in Example 4, demonstrate that even higher amounts of product can be obtained if the Exo I digest step is included (as shown by the amount and distribution of material in the experimental lanes (20 ng) instead of the control lanes (0 ng) compared to the results in FIG. 11).

EXAMPLE 8

Exo I Treatment Post WGA Procedure

This example demonstrates one embodiment in which the cleaning step (e.g., Exo I treatment) is performed later in the procedure (after the "further extension and pre-PCR"). The specifics of the protocol are outlined in Table 7.

TABLE 7

| Whole genome Amplification | stock concentrations (uM) | final concentration (uM) | Final Concentration |
|---|---|---|---|
| step 1 extension and pre-PCR | volumes (uL) | | |
| 10xPCR buffer II | 2 | 10 | 1 |
| DNA-template | 4 | 0 | 0 |
| N8-UR-T10 (100 uM) | 2 | 100 | 10 | (10 uM) |
| AmpliTaq 5 u/ul | 4 | 5 | 1 | (1 Unit/ul) |
| dNTP 100 mM | 1 | 100 | 5 | (5 mM) |
| MgCl2 25 mM | 2.4 | 25 | 3 | (3.0 mM) |
| H2O | 4.6 | | |
| total volume | 20 | | |
| 95 C 5 min | | | |
| (95 C 30 sec –35 C 2 min –65 C 2 min) 20 cycles | | | |
| step 2 further extension and pre-PCR | | | |
| 10xPCRbuffer II | 4 | 10 | 1 |
| above reagent | 20 | | 0 |
| UR-T10 100 uM | 4 | 100 | 10 | (10 uM) |
| dNTP 100 mM | 1 | 100 | 2.5 | (2.5 mM) |
| MgCl2 25 mM | 2.4 | 25 | 1.5 | (15 mM) |
| AmpliTaq 5 u/ul | 2.6 | 5 | 0.325 | (0.325 u/ul) |
| H2O | 6 | | 0 |
| total volume | 40 | | |
| 95 C 1 min | | | |
| (95 C 30 sec –65 C 1 min –72 C 2 min) 30x | | | |
| step 3 PCR clean up | | | |
| 10 ul above product + 2 ul ExoSAP | | | |
| 37 C 15 min, 85 C 5 min | | | |
| above 10 ul product load on the gel | | | |

Figure 13:
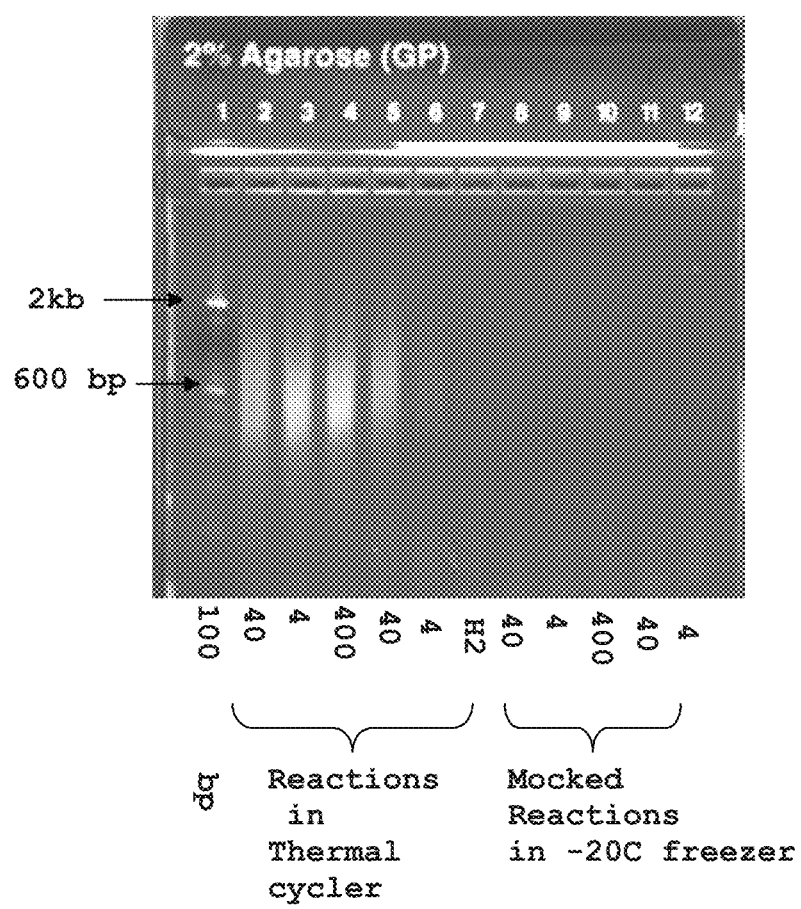
FIG. 13 is a depiction of a gel demonstrating that amplification was achieved under a variety of conditions.

The results of these initial rounds of amplification are shown in FIG. 13. As shown in the gel in FIG. 13, substantially large sections of the target nucleic acid were amplified (as shown by the relatively high weight of the amplified product, with most of the smear falling between 200 bp to 2 kb in the appropriate lanes). Additionally, these results further demonstrate that even for the smaller amounts of initial sample, an appropriately scaled amount of final product can be achieved (e.g., 4 pg of starting material resulted in a correspondingly smaller amount of final product than 40 pg and 40 pg resulted in a correspondingly smaller amount than 400, etc.). These results further demonstrate that the use of these loopable primers can readily result in highly efficient amplification of very low starting samples (e.g., 4 pg shows up on the gel) with a desired sized amplification product (e.g., between 200 bp and 2 kb and a large amount of amplification around the 400 to 800 bp range).

Following the Exo I nuclease digestion, insert amplification primers for RNase P were added in a TAQMAN™ assay in order to demonstrate the additional step of insert amplification and to demonstrate the amplification abilities of the technique. The results are shown in Table 8.

As shown in amplification results in Table 8, the use of the Exo I nuclease cleaning step following the extension and pre-PCR steps resulted in a substantial increase in the amplification fold of the target nucleic acid sequence. As shown above, using this embodiment resulted in more than an 800,000 fold amplification when starting with 400 pg of target nucleic acid.

It is noted that the apparent increase in amplification fold (from 40 ng to 400 pg) is likely due to the higher starting amounts already being saturating (as they all have a similar Ct). Similarly, it is noted that the lower amplification amounts (from the 40 pg to 4 pg) is likely due to the relatively higher amount of intrinsic variation that can occur when such small starting samples are used.

EXAMPLE 9

Varied Number of PCR Cycles in Step 2

This example demonstrates how varying the number of cycles in step 2 of the PCR protocol (in Example 8) can produce various results that are consistent with the teachings herein. The example demonstrates that varying the number of cycles can improve the final yield of the protocol.

TABLE 8

| Rnase P Assay CEPH gDNA | N8-T10-RP real (Ct) | N8-T10-RP real (SD) | N8-T10-RP mocked (Ct) | N8-T10-RP mocked (SD) | Amplification Folds | SD |
|---|---|---|---|---|---|---|
| 40 ng | 17.60 | 0.03 | 29.08 | 0.38 | 2904 | 816 |
| 4 ng | 17.05 | 0.11 | 32.23 | 0.42 | 38237 | 13558 |
| 400 pg | 16.16 | 0.09 | 35.54 | 1.33 | 812717 | 624835 |
| 40 pg | 17.97 | 0.04 | 37.02 | 1.37 | 675933 | 569503 |
| 4 pg | 24.23 | 0.18 | 36.84 | 0.11 | 6289 | 303 |
| NTC | 37.17 | 0.44 | 40.00 | 0.00 | 7 | 2 |

Additionally, the example demonstrates that varying the number of cycles can also maintain or result in a better dose response. The impact of varying the number of cycles in step 2 was examined for the protocol disclosed in Example 8, including 14, 20, 25, and 30 cycles. The results are presented in FIG. 14 and Tables 9 and 10.

Figure 14:
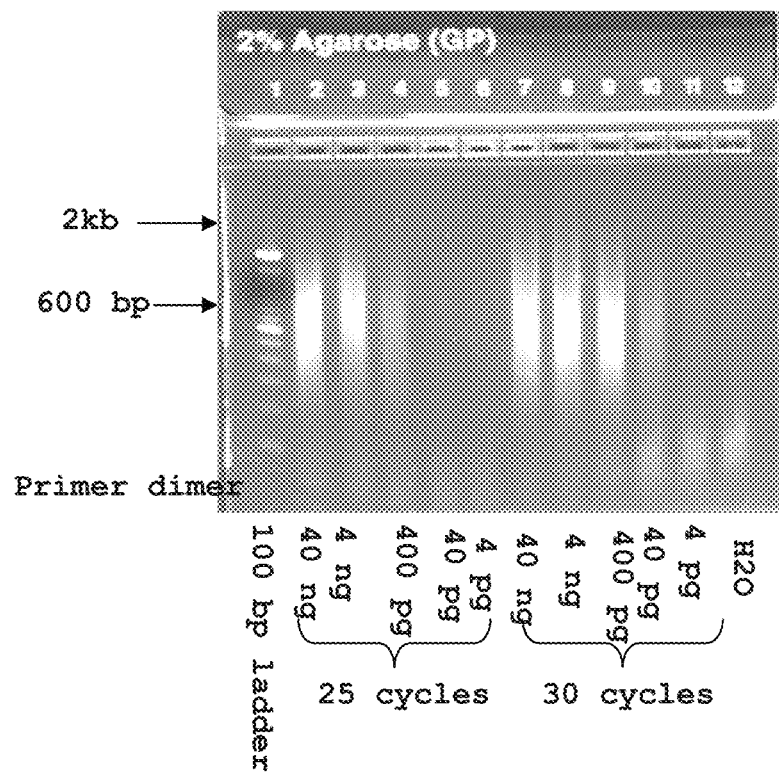
FIG. 14 is a depiction of a gel demonstrating that amplification was achieved under a variety of conditions.

As can be observed in the gel depicted in FIG. 14, 25 cycles in step 2 resulted in observable amplification for 40 pg, 400 pg, 4 ng, and 40 ng. Additionally, the amplification at these ranges did not saturate; thus, for this range of concentration of target nucleic acid sequence, amplification can be readily achieved while maintaining appropriate relative concentrations between various target nucleic acid sequences. Furthermore, one can observe that, while there is some apparent saturation for 30 cycles, amplification was appropriate and maintained its relative distribution for at least the 40 pg to 400 pg range.

TABLE 9

| Rnase P Assay CEPH gDNA | N8-T10-RP step 2 × 14 (Ct) | N8-T10-RP SD | N8-T10-RP Step 2 × 20 (Ct) | N8-T10-RP SD |
|---|---|---|---|---|
| 40 ng | 26.98 | 0.22 | 22.41 | 0.11 |
| 4 ng | 27.98 | 0.32 | 23.00 | 0.13 |
| 400 pg | 29.47 | 0.22 | 24.94 | 0.11 |
| 40 pg | 35.59 | 0.01 | 29.26 | 0.03 |
| 4 pg | 37.12 | 0.82 | 36.13 | 0.73 |
| NTC | 38.81 | 1.68 | 39.62 | 0.53 |

TABLE 10

| Rnase P Assay CEPH gDNA | N8-T10-RP step 2 × 14 (Ct) | N8-T10-RP SD | N8-T10-RP Step 2 × 20 (Ct) | N8-T10-RP SD |
|---|---|---|---|---|
| 40 ng | 18.61 | 0.06 | 15.72 | 0.37 |
| 4 ng | 18.65 | 0.36 | 15.63 | 0.08 |
| 400 pg | 20.10 | 0.06 | 15.15 | 0.22 |
| 40 pg | 34.24 | 0.45 | 17.84 | 0.11 |
| 4 pg | 34.01 | 0.30 | 34.58 | 0.38 |
| NTC | 34.15 | 0.20 | 33.92 | 0.36 |

As can be observed in the results presented in Tables 9 and 10, increasing the number of cycles resulted in a larger increase in the amount of final product (noted by the decrease in the Ct). Additionally, the results generally demonstrate that, by using varying cycle numbers, one can amplify varying amounts of initial target nucleic acid sequence, while maintaining the relative ratios of the various target nucleic acid sequences. Furthermore, the above results generally provide guidance as to what initial cycle number should be used when amplifying the various ranges of initial target nucleic acid sequence. Of course, these numbers can be routinely optimized with the disclosure presented herein.

EXAMPLE 10

RNA Amplification

This example demonstrates one application for some of the present embodiments for RNA amplification. The protocol for the first 4 steps (prior to the insert amplification) is generally outlined in Table 11.

TABLE 11

| Whole genome Amplification | stock concentrations (uM) | Final concentration (uM) | Final Concentration |
|---|---|---|---|
| step 1 Random primer RT | | | |
| 10x cDNA Archiving Kit buffer | 0.50 | 10 | 1 | 1x |
| MMLV 50 u/ul | 0.50 | 50 | 5 | 5 U/uL |
| 100 mM dNTP | 0.25 | 100 | 5 | (5 mM) |
| 10x random primers (100 uM) | 0.50 | 10 | 10 | (10 uM) |
| HL total RNA 40 ng-4 pg | 2.00 | | | |
| MgCl2 25 mM | 0.60 | 25 | 3 | 3.0 mM/uL |
| H2O | 0.65 | | | |
| total volume | 5.00 | | | |
| RT 25 C 10 min, 37 C 120 min, 85 C 5 min | | | | |
| step 2 extension and pre-PCR | volumes (uL) | | | |
| 10xPCR buffer II | 2 | 10 | 1 | 1x |
| RT products clean up | 6 | 0 | 0 | |
| NB-UR-TIO) (100 uM) | 2 | 100 | 10 | (10 uM) |
| AmpliTaq 5 u/ul | 4 | 5 | 1 | (1 Unit/ul) |
| dNTP 100 mM | 1 | 100 | 5 | (5 mM) |
| MgCl2 25 mM | 2.4 | 25 | 3 | (3.0 mM) |
| H2O | 2.6 | 0 | 0 | |
| total volume | 20 | | | |
| 95 C 1 min | | | | |
| (95 C 30 sec –35 C 2 min –65 C 2 min) 20 cycles | | | | |
| step 3 further extension and pre-PCR | | | | |
| 10xPCRbuffer II | 4 | 10 | 1 | 1x |
| above reagent | 20 | 0 | | |
| UR-TIO 100 uM | 4 | 100 | 10 | (10 uM) |
| dNTP 100 mM | 1 | 100 | 2.5 | (2.5 mM) |
| MgCl2 25 mM | 2.4 | 25 | 1.5 | (1.5 mM) |
| AmpliTaq 5 u/ul | 4 | 5 | 0.5 | (0.5 u/ul) |
| H2O | 4.6 | 0 | | |
| total volume | 40 | | | |
| 95 C 1 min | | | | |
| (95 C 30 sec –65 C 1 min –72 C 2 min) 30x | | | | |
| step 4 PCR clean up | | | | |

TABLE 11-continued

| Whole genome Amplification | stock concentrations (uM) | Final concentration (uM) | Final Concentration |
|---|---|---|---|
| 10 ul above product + 2 ul ExoSAP 37 C 15 min, 85 C 5 min above 10 ul product load on the gel or 2 uL to run RNAse P TaqMan assay | | | |

Figure 15:
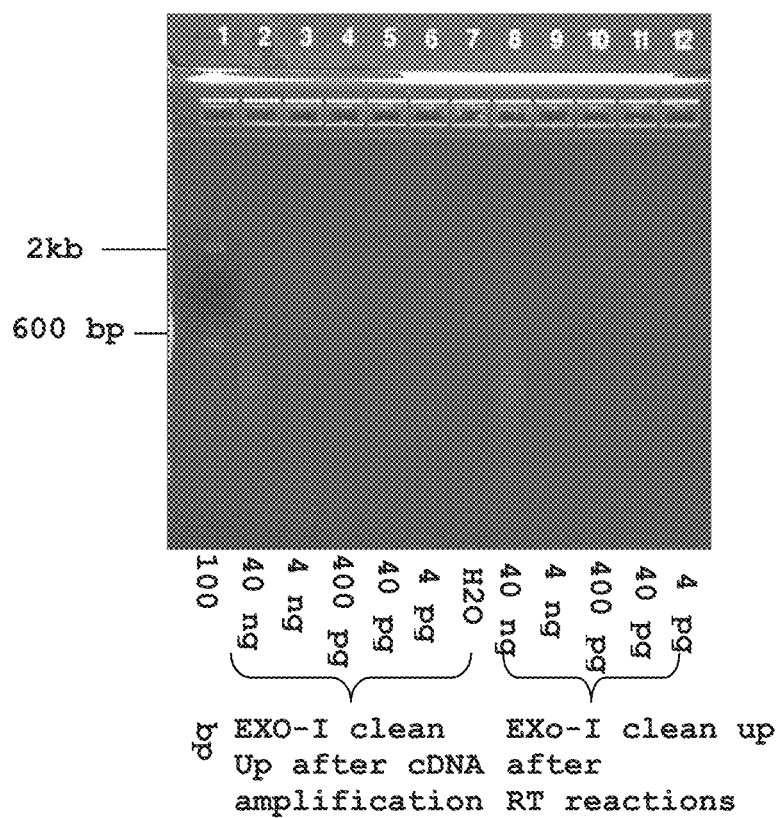
FIG. 15 is a depiction of a gel demonstrating that amplification was achieved under a variety of conditions.

As shown in Table 11, when one wishes to amplify RNA instead of gDNA, one can add an initial step (step 1) for reverse transcription. In step 1 of the present example, random primer reverse transcription was initially performed on the target sample. Following this, a similar set of protocols (as in Example 8) was performed on the starting sample. The results are displayed in FIG. 15. As shown in FIG. 15, the desired smears in the appropriate lanes demonstrate the expected amplification of the relatively large sections of target nucleic acid sequence (incorporated in the double-extended loopable primer).

As in some of the above examples, the amplified product (double-extended loopable primer) was then used for further, selective amplification via the insert amplification primers for RNase P, via a TAQMAN™ assay for RNase P. The results from this experiment are displayed in Table 12.

TABLE 12

| Rnase P Assay Human lung RNA | N8-T10-RP Ct values no Exo after step 1 | N8-T10-RP SD no Exo after step 1 | N8-T10-RP Ct values no Exo after step 1 | N8-T10-RP SD no Exo after step 1 |
|---|---|---|---|---|
| 40 ng | 15.08 | 0.08 | 15.37 | 0.09 |
| 4 ng | 18.10 | 0.03 | 23.10 | 0.16 |
| 400 pg | 17.41 | 0.01 | 25.02 | 0.01 |
| 40 pg | 24.43 | 0.08 | 28.82 | 0.25 |
| 4 pg | 27.73 | 0.46 | 33.03 | 0.18 |
| NTC | 33.63 | 0.03 | 37.32 | 3.80 |

As demonstrated in the results above, the technique clearly functioned for RNA amplification. Furthermore, as shown in the second column of Table 12, even starting amounts as low as 4 pg resulted in significant amounts of final product (e.g., under 30 Ct).

Additionally, the results in Table 12 further presents data that compares the impact of including an EXO I digestion step after step 1 or not. As can be seen from the data, a substantial amount of amplification occurred with or without an Exo I step after step 1. Surprisingly, it was found that adding the Exo I step, after the first step (step 1) decreased the resulting amount of product.

In light of the above, it appears that the EXO I step can be especially beneficial when used following the single primer amplification. This was surprising because the use of the EXO I step at an earlier stage (following the first step) was not as effective.

EXAMPLE 11

Insert Amplification--Primer Pools

As will be appreciated by one of skill in the art, in many of the embodiments described above, insert amplification can be achieved based on knowing which sequence was (or should be) contained within the loop, such as RNase P. In situations in which the target within the insert section is not initially known, such as when an entire genome is being amplified, the protocol can be varied slightly to take this variable into account. For example, indiscriminant primers could be used. Alternatively, and as described in this example, numerous primers can be tested or used on the amplified sample.

Following any of the above initial amplification procedures (e.g. at a point following the formation of the double-extended loopable primer, but prior to the use of an insert amplification primer) one can divide the amplified product into numerous subsamples. Each subsample will simply be a fraction of the amplified product, and thus can include a representative (e.g. proportionate and substantially complete) distribution of the various double-extended loopable primers. Each subsample can be placed in a separate well, to which a specific known, or knowable, insert amplification primer, or primers, can be added. Following this, an amplification step can be performed in each of the wells. This will allow for the amplification of the looped section of the self-hybridized double-extended loopable primer. These amplified sequences can then be detected, such as by sequencing.

EXAMPLE 12

STR Amplification

The present example demonstrates how one can use the methods and primers described herein to amplify a STR locus of interest.

At least one loopable primer, having a 3' target specific region that will bind near a locus to be examined, is combined with a sample that includes a target nucleic acid sequence. The 3' target specific region can be selected so that it binds near at least one of the following loci: TH01, TPOX, CSF1PO, vWA, FGA, D3S1358, D5S818, D7S820, D13S317, D16S539, D8S1179, D18S51, D21S11, D2S1338, D3S1539, D4S2368, D9S930, D10S1239, D14S118, D14S548, D14S562, D16S490, D16S753, D17S1298, D17S1299, D19S253, D19S433, D20S481, D22S683, HUMCSF1PO, HUMTPOX, HUMTH01, HUMF13AO1, HUMBFXIII, HUMLIPOL, HUMvWFA31, Amelogenin, D12s391, D6S1043, SE33, or any combination thereof. The amplification outlined in any of the above examples or embodiments can be performed, thereby resulting in the amplification of the relevant locus.

EXAMPLE 13

STR Amplification

The present example demonstrates how one can use the methods and primers described herein to amplify a STR locus of interest.

At least one loopable primer, having a 3' target specific region that comprises a degenerate region, is combined with a sample that includes a target nucleic acid sequence. The loopable primer is used to amplify the target nucleic acid sequence as provided in any of the above examples. However, once the double extended loopable primer is created, the insert amplification primers that are used are selected so that the insert amplification primers bind near at least one of the following loci: TH01, TPOX, CSF1PO, vWA, FGA, D3S1358, D5S818, D7S820, D13S317, D16S539, D8S1179, D18S51, D21S11, D2S1338, D3S1539, D4S2368, D9S930, D10S1239, D14S118, D14S548, D14S562, D16S490, D16S753, D17S1298, D17S1299, D19S253, D19S433, D20S481, D22S683, HUMCSF1PO, HUMTPOX, HUMTH01, HUMF13AO1, HUMBFXIII, HUMLIPOL, HUMvWFA31, Amelogenin, D12s391, D6S1043, and SE33. This will then allow for the amplification of the STR at the relevant locus.

As will be appreciated by one of skill in the art, numerous insert amplification primers can be used for the above processing, e.g. 2-10, 10-50, 50-100, 100-1000, 1000-10,000, 10,000-30,000, 30,000-40,000, 40,000-50,000, 50,000-100,000, or more primers. Each can be used in a separate well with a representative portion of the amplified target nucleic acid sequence. As will be appreciated by one of skill in the art, during the amplification, the conditions should be such that the double-extended loopable primer is self-hybridized, resulting in the selective amplification of the initially amplified products of the desired size.

The above results clearly establish that the presently disclosed processes can be effective in selectively amplifying usefully sized fragments throughout relatively long stretches of gDNA from a target sample. While the above embodiments have been described in terms of a loopable primer, in other embodiments, the initial primer can be linear or need not be loopable (as long as there is a universal region that is placed on one end and its complement is placed on the other end of a section of nucleic acid to be amplified). Thus, in some embodiments, any or every one of the above embodiments can be used with a linear primer instead of a loopable primer.

Furthermore, in some embodiments, the amount of amplification is, compared to the current state of the art, very high (approximately 3000 fold to over hundreds of thousands fold), while still amplifying the larger fragments. This is in contrast to previous attempts at amplification using random primers that appeared to generally reach lower levels of amplification. (See, e.g. Zhang et al., PNAS, vol. 89, 5847-5851, (1992), approximately 30 fold; and Genomeplex™ Whole Genome Amplification (WGA) Kit by Sigma-Aldrich, discussed on the world wide web at biocompare.com/review/769/Genomeplex-Whole-Genome-Amplification-(WGA)-Kit--by-Sigma-Aldrich.html, discussing 3000 fold). Additionally, as shown above, the amplification ability can be enhanced through the use of an Exo I digestion step, although this is clearly not required. It is believed that these data demonstrate that 3' target-specific portions (e.g., degenerate regions) of 7-15 nucleic acids in length will work for some embodiments. Additionally, in some embodiments these relatively large increases in amplification are achieved while still maintaining some degree of dose response during the amplification. For example, in some embodiments, relatively small amounts of one species to be amplified will still be a relatively small percent of the amplified product (although it could have been amplified, e.g. 100-1,000,000 times).

In this disclosure, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments. The phrase "and/or" denotes a shorthand way of indicating that the specific combination is contemplated in combination and, separately, in the alternative.

The section headings used herein are for organizational purposes only and are not to be construed as limiting the described subject matter in any way.

It will be appreciated that there is an implied "about" prior to the temperatures, concentrations, times, etc. discussed in the present teachings, such that slight and insubstantial deviations are within the scope of the present teachings herein. For example, "a primer" means that more than one primer can, but need not, be present; for example but without limitation, one or more copies of a particular primer species, as well as one or more versions of a particular primer type, for example but not limited to, a multiplicity of different loopable primers. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the invention.

Unless specifically noted in the above specification, embodiments in the above specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

INCORPORATION BY REFERENCE

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application; including but not limited to defined terms, term usage, described techniques, or the like, this application controls.

EQUIVALENTS

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A multiplex amplification reaction mixture comprising:
   a) a nucleic acid sample having a plurality of different target nucleic acids; and
   b) a mixture of two or more different loopable primers, each loopable primer including a single-stranded nucleic acid molecule having in a 3' to 5' direction
      (i) a single-stranded target-specific 3' region;
      (ii) a first loop-forming region which forms a first strand of a double-stranded stem region;
      (iii) a non-complementary region and a universal priming region which forms a single-stranded loop;
      (iv) a second loop-forming region which forms a second strand of the double-stranded stem region; and
      (v) a non-complementary single-stranded 5' tail,
   wherein the single-stranded target specific 3' region includes at least one inosine,
   wherein the first and the second loop-forming regions hybridize to each other to form a double-stranded stem region,
   wherein the single-stranded loop is located between the first and second loop-forming regions, and the non-complementary region of (iii) contains only adenine residues,
   wherein the two or more different loopable primers have non-complementary single-stranded 5' tails containing different identification sequences, and
   wherein the stem and the loop, when formed, are configured to allow the single-stranded target specific 3' region to hybridize to a target nucleic acid without the target nucleic acid hybridizing to the double-stranded stem, the non-complementary region of (iii) or the non-complementary 5' tail.

2. The multiplex amplification reaction mixture of claim 1, wherein the single-stranded target-specific 3' region comprises a nucleotide sequence that can hybridize to a desired short tandem repeat.

3. The multiplex amplification reaction mixture of claim 1, wherein the single-stranded target-specific 3' region comprises a nucleotide sequence that can hybridize to a locus selected from one or more of the group consisting of: TH01, TPOX, CSF1PO, vWA, FGA, D3S1358, D5S818, D7S820, D13S317, D16S539, D8S1179, D18S51, D21S11, D2S1338, D3S1539, D4S2368, D9S930, D10S1239, D14S118, D14S548, D14S562, D16S490, D16S753, D17S1298, D17S1299, D19S253, D19S433, D20S481, D22S683, HUMCSF1PO, HUMTPOX, HUMTH01, HUMF13AO1, HUMBFXIII, HUMLIPOL, HUMvWFA31, Amelogenin, D12s391, D6S1043, SE33, or any combination thereof.

4. The multiplex amplification reaction mixture of claim 1, wherein the mixture of two or more different loopable primers includes a first loopable primer and a second loopable primer having different sequences that form their respective double-stranded stem regions.

5. The multiplex amplification reaction mixture of claim 1, wherein the nucleic acid sample comprises DNA or RNA.

6. The multiplex amplification reaction mixture of claim 1, further comprising a polymerase or reverse transcriptase.

* * * * *